United States Patent
Middleton

(10) Patent No.: US 7,488,320 B2
(45) Date of Patent: Feb. 10, 2009

(54) ORTHOPAEDIC IMPLANT FIXATION USING AN IN-SITU FORMED ANCHOR

(75) Inventor: Lance M. Middleton, Trumbull, CT (US)

(73) Assignee: Renova Orthopedics, LLC, Oklahoma City, OK (US)

( * ) Notice: Subject to any disclaimer, the term of this patent is extended or adjusted under 35 U.S.C. 154(b) by 243 days.

(21) Appl. No.: 10/284,672

(22) Filed: Oct. 31, 2002

(65) Prior Publication Data

US 2003/0083662 A1  May 1, 2003

Related U.S. Application Data

(60) Provisional application No. 60/336,557, filed on Nov. 1, 2001.

(51) Int. Cl.
*A61B 17/56* (2006.01)

(52) U.S. Cl. .............................. 606/62; 606/323; 606/92

(58) Field of Classification Search ............. 606/72–73, 606/92–94, 62, 64–68, 300, 309–310, 323, 606/76, 910
See application file for complete search history.

(56) References Cited

U.S. PATENT DOCUMENTS

| | | | |
|---|---|---|---|
| 4,065,817 A | | 1/1978 | Branemark et al. |
| 4,369,772 A | | 1/1983 | Miller |
| 4,494,535 A | * | 1/1985 | Haig ........................... 606/67 |
| 4,653,489 A | * | 3/1987 | Tronzo ........................ 606/65 |
| 4,893,974 A | * | 1/1990 | Fischer et al. .............. 411/82.1 |
| 5,514,137 A | | 5/1996 | Coutts |
| 5,665,110 A | | 9/1997 | Chervitz et al. |
| 5,743,912 A | * | 4/1998 | Lahille et al. ................. 606/65 |
| 5,928,239 A | | 7/1999 | Mirza |
| 5,990,194 A | | 11/1999 | Dunn et al. |
| 6,048,343 A | | 4/2000 | Mathis et al. |
| 6,210,376 B1 | | 4/2001 | Grayson |
| 6,214,012 B1 | * | 4/2001 | Karpman et al. .............. 606/93 |
| 6,264,659 B1 | | 7/2001 | Ross et al. |
| 6,375,659 B1 | * | 4/2002 | Erbe et al. .................... 606/94 |
| 6,447,514 B1 | * | 9/2002 | Stalcup et al. ................ 606/63 |
| 6,558,386 B1 | | 5/2003 | Cragg |
| 6,558,390 B2 | | 5/2003 | Cragg |
| 6,575,979 B1 | | 6/2003 | Cragg |
| 6,740,090 B1 | | 5/2004 | Cragg et al. |
| 6,790,210 B1 | | 9/2004 | Cragg et al. |
| 7,014,633 B2 | | 3/2006 | Cragg |
| 2001/0021852 A1 | * | 9/2001 | Chappius ..................... 606/73 |
| 2002/0016583 A1 | | 2/2002 | Cragg |
| 2002/0116064 A1 | | 8/2002 | Middleton |
| 2003/0191474 A1 | | 10/2003 | Cragg et al. |

\* cited by examiner

*Primary Examiner*—Eduardo C Robert
*Assistant Examiner*—James L Swiger, III
(74) *Attorney, Agent, or Firm*—Gardere Wynne Sewell, LLP

(57) ABSTRACT

An orthopaedic implant fixation using a surgically created bone cavity as a mold for forming an anchor from an in-situ hardenable material. An in-situ formed anchor of the present invention is especially useful for attaching an implant to osteoporotic cancellous bone. The injectable nature of the in-situ formed anchor allows implants to be adapted to minimally invasive surgical techniques. The present invention can be adapted to numerous implants or implant system components to include fasteners, pins, nails, intramedullary nails, and suture anchors. Applications include bone fracture fixation, bone fracture prevention, and soft-tissue repair.

26 Claims, 22 Drawing Sheets

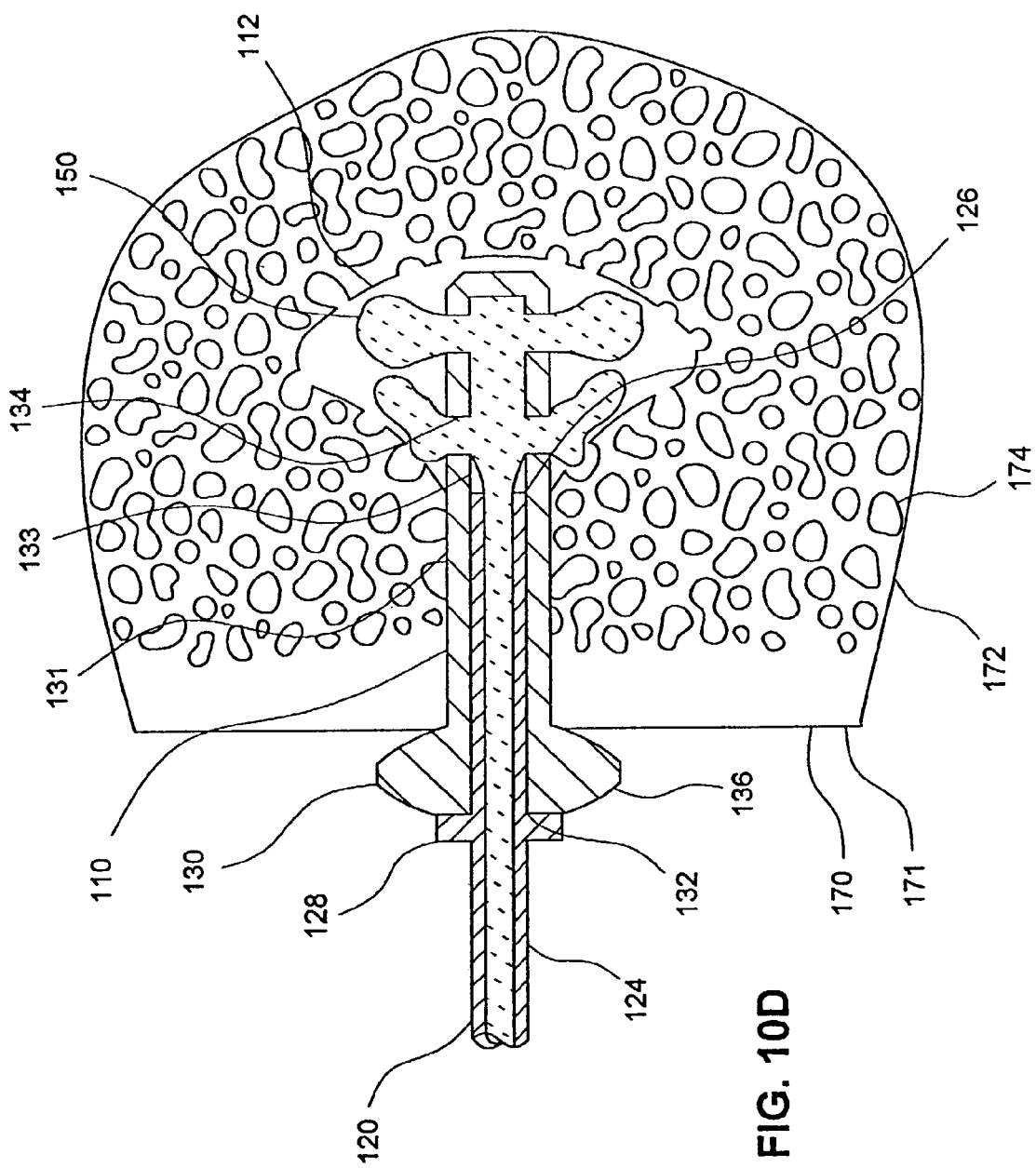

ORTHOPAEDIC IMPLANT FIXATION USING AN IN-SITU FORMED ANCHOR

CROSS-REFERENCE TO RELATED APPLICATIONS

This application claims the priority of U.S. Provisional Patent Application Ser. No. 60/336,557 filed Nov. 1, 2001.

FIELD OF THE INVENTION

The present invention generally relates to orthopaedic implants and, more particularly, to fixation of orthopaedic implants to bone.

BACKGROUND OF THE INVENTION

Bone structures are typically comprised of two types of bone, cortical bone and cancellous bone. Cortical bone can be characterized as a rigid and dense material, whereas cancellous bone can be characterized as a structured material with a high degree of visible porosity. Cortical bone and cancellous bone combine to form structures that are strong and lightweight. However, strength can be compromised by osteoporosis, a metabolic disease characterized by a decrease in bone mass. It is estimated that osteoporosis affects approximately 15-20 million people in the United States. Although osteoporosis can affect persons of all ages and both genders, it is generally a disease associated with the elderly. Approximately 1.3 million new fractures each year are associated with osteoporosis, and the most common fracture sites are the hip, wrist and vertebrae. Osteoporosis leads to skeletal fractures under light to moderate trauma and, in its advanced state, can lead to fractures under normal physiologic loading conditions.

Whether treating a fracture associated with osteoporosis or another disorder of the musculoskeletal system, implant attachment to weakened osteoporotic bone can be problematic. Inadequate attachment of an orthopaedic implant to osteoporotic bone can result in less effective, or ineffective implant fixation.

Generally, orthopaedic implant fixation is accomplished by numerous conventional attachment mechanisms to include screw thread, serration, spikes, barbs, porous coatings, and treated surfaces. Some attachment mechanisms expand within bone, analogous to a rivet or wall anchor. Bone cements are also used for orthopaedic implant fixation, primarily as an adhesive interface layer between implant and bone. Bone cement can also be used to augment cancellous bone adjacent to an attachment region, wherein bone cement is used to fill or partially fill cancellous bone pores.

A common approach to implant fixation is the screw thread, used on implants such as bone screws. Bone screws can be used as stand-alone devices for attaching fractured bone or used in a multi-component implant assembly. Tightening bone screws is generally subjective and the appropriate fixation is especially difficult to judge when securing a bone screw to osteoporotic cancellous bone. Over-tightening can lead to stripping of bone and inadequate fixation, while under-tightening can also lead to inadequate fixation. After a screw has failed to hold, bone cement can be used to augment screw fixation by filling a drilled hole with the bone cement, or by coating the screw thread with bone cement prior to reinsertion. These time consuming repair techniques have experienced some success; however, the necessity for repair emphasizes the potential ineffectiveness of screw thread purchase in osteoporotic bone. Also, bone screws can occasionally loosen, losing their effectiveness. Further, loose bone screws can ultimately back-out and migrate to an undesirable position or location.

There are numerous examples of orthopaedic implants that serve as conduits for the delivery of synthetic material, usually bone cement, to specific bone/implant interface regions. Cannulated bone screws adapted with screw thread apertures for the delivery of bone cement are described in U.S. Pat. No. 4,653,489 to Tronzo, U.S. Pat. No. 6,048,343 to Mathis et. al., U.S. Pat. No. 6,210,376 to Grayson, and U.S. Pat. No. 6,214,012, to Karpmen et. al. Foremost, the addition of apertures to a screw thread substantially weakens the bone screw. Another disadvantage is the potential for uneven distribution of bone cement within cancellous bone, caused in part by bone pore regions not directly adjacent to apertures receiving a disproportionate amount of the injected cement. In addition, extruding directly into bone can require relatively high pressures depending on the bone characteristics and the viscosity of the injectable material. Injection at lower pressure is preferred because simpler injection systems can be used and migration of injectable material is less likely.

There are known concepts of non-threaded orthopaedic implants serving as conduits for the delivery of bone cement, or other materials for implant fixation. Examples include implant fixation within an intramedullary canal, such as an intramedullary nail used for fracture fixation. For example, U.S. Pat. No. 4,369,772 to Miller describes a method for strengthening a fractured femur which comprises drilling a hole along the axis of the medullary canal of the bone, inserting in the hole a substantially inflexible tube having an outside diameter less than the diameter of the hole, injecting into the tube and around the tube a semisolid hardenable bone cement, and allowing time for the mixture to harden. U.S. Pat. No. 5,514,137 to Coutts describes a cannulated intramedullary nail adapted for the extrusion of resorbable bone cement from the distal tip in order to augment cancellous bone in the distal region of the nail.

Another mechanism for attaching an implant to bone is disclosed in U.S. Pat. No. 4,065,817 to Branemark. The implant described in the patent to Branemark is formed as a tubular support member having perforations therein, the end of the bone is bored, the tubular member is introduced into the bore and cement is introduced into the interior of the tubular support and passes out through the perforations to provide the midterm anchor on the walls of the bone.

A need exists to develop improved implant fixation to bone, and in particular, implant fixation to osteoporotic bone. Preferably, inventions to improve implant fixation to bone should be applicable to a wide range of implant systems, and also be readily adaptable to minimally invasive surgical techniques.

SUMMARY OF THE INVENTION

Accordingly, the present invention is directed toward improved fixation of an implant to bone, especially implant fixation to osteoporotic bone. The present invention accomplishes orthopaedic implant fixation by using a surgically created bone cavity as a mold for forming an anchor from an in-situ hardenable material. An implant of the present invention includes a preformed element and an in-situ formed anchor.

A preferred embodiment of the present invention includes a surgically created pilot hole and bone cavity. The steps generally include drilling a pilot hole, and using the pilot hole to access a location for forming a bone cavity. The pilot hole is sized for passage and support of the preformed element.

The bone cavity has a significantly larger diameter than the pilot hole, and a specific shape and size are created to form a mold for the in-situ formed anchor.

Minimally invasive devices and methods for forming a pilot hole and bone cavity have been developed and are disclosed in Applicant's co-pending application Ser. No. 09/872,042, which is hereby incorporated by reference.

The preformed element is preferably adapted with structures or voids for interlocking with the in-situ formed anchor. A suitable in-situ hardenable material, in an injectable state, can flow through, into, and around the structures or voids of a preformed element in an interlocking manner. Therefore, an in-situ formed anchor is securely attached to the preformed element following hardening of the in-situ hardenable material. Similarly, in-situ hardenable material can fill or partially fill cancellous bone pores adjacent to the in-situ formed anchor, forming an anchor-bone interlock. Compared to traditional attachment mechanisms, such as, screw threads, the in-situ formed anchor is relatively large, creating a broad and secure foundation for implant fixation that is further supported by the anchor-bone interlocks.

A wide range of in-situ hardenable materials can be used to form an in-situ formed anchor, including common polymethylmethacrylate-based bone cements. However, preferred injectable in-situ hardening materials include load-bearing polymers and synthetic bone substitutes, such as injectable calcium phosphates.

A fundamental approach to minimally invasive surgery is the percutaneous passage of instruments and implants through small tubes and cannula. As previously mentioned, minimally invasive devices and methods for creating a pilot hole and bone cavity have been developed. Also, since the in-situ formed anchor is injected, it is possible to adapt the present invention to minimally invasive techniques.

The present invention is also advantageous because relatively low pressures are required to fill a relatively large bone cavity with an in-situ hardenable material. This will result in the effective use of a wide range of in-situ hardenable materials to include materials with higher injection viscosity. Lower pressures result in improved injection over a greater distances, injection through smaller diameter tubes and needles, and the potential for simpler, low-pressure injection systems, such as syringes. In addition, lower pressure results in a decreased likelihood of detrimental migration of in-situ hardenable material to unintended areas.

The advantages of the present invention include simplicity, as a bone cavity can be used as a mold to form an uncomplicated anchor interlocked to a preformed element. The present invention can be applied to numerous implants or implant system components to include, but not limited to, fasteners, pins, nails, intramedullary nails, and suture anchors. Applications include bone fracture fixation, bone fracture prevention, and soft-tissue repair. These and additional advantages will become evident from a consideration of the following description and drawings.

BRIEF DESCRIPTION OF THE DRAWINGS

FIGS. 10A to 10E are in-situ sectional views depicting a first preferred method of implanting the bone fastener depicted in FIGS. 1B to 1C.

DETAILED DESCRIPTION OF THE PREFERRED EMBODIMENTS

Figure 1A:
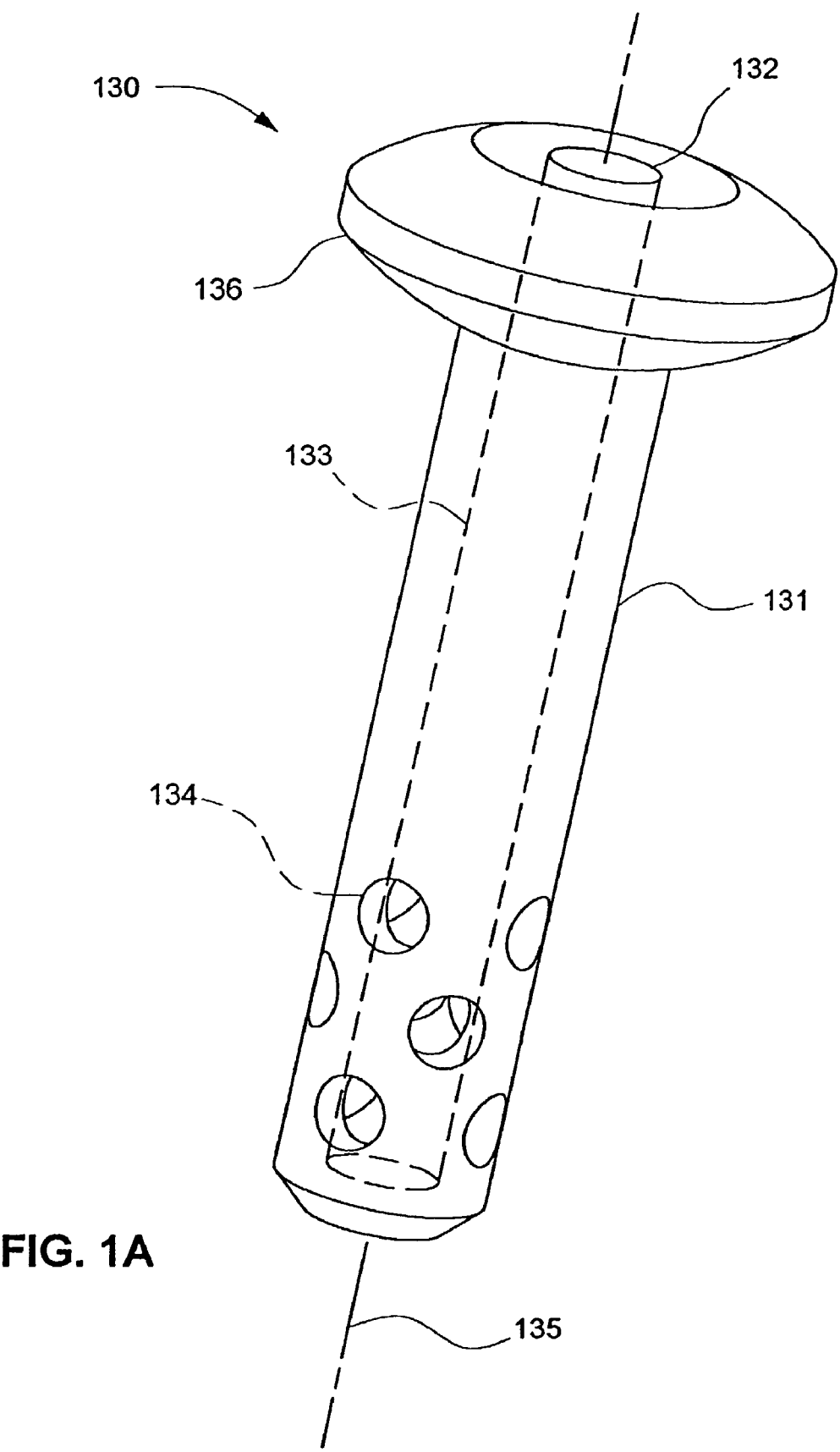
FIG. 1A is a perspective view of a preformed element.

Throughout the following description and the drawings, like reference numerals are used to identify like parts of the present invention. The term "proximal", as is traditional, will refer to the portion of the structure which is closer to the operator while the term "distal" will refer to the portion which is further from the operator.

Numerous orthopaedic implants are broadly categorized as bone fasteners, to include screws, pins, and nails. These implants, pervasive in orthopaedic surgery, can be used as stand-alone devices to attach fractured or fragmented bone, or bone fasteners can be used as a component in an assembly or construct, such as a bone plate and screw construct. In order to focus on the spirit of the invention, the preferred embodiments of the present invention called bone fasteners will generally be shown as a stand-alone device without additional implant components and, further, without a reference to a specific application. Those skilled in the art will appreciate the wide variety of uses and applications of bone fasteners.

Figure 1B:
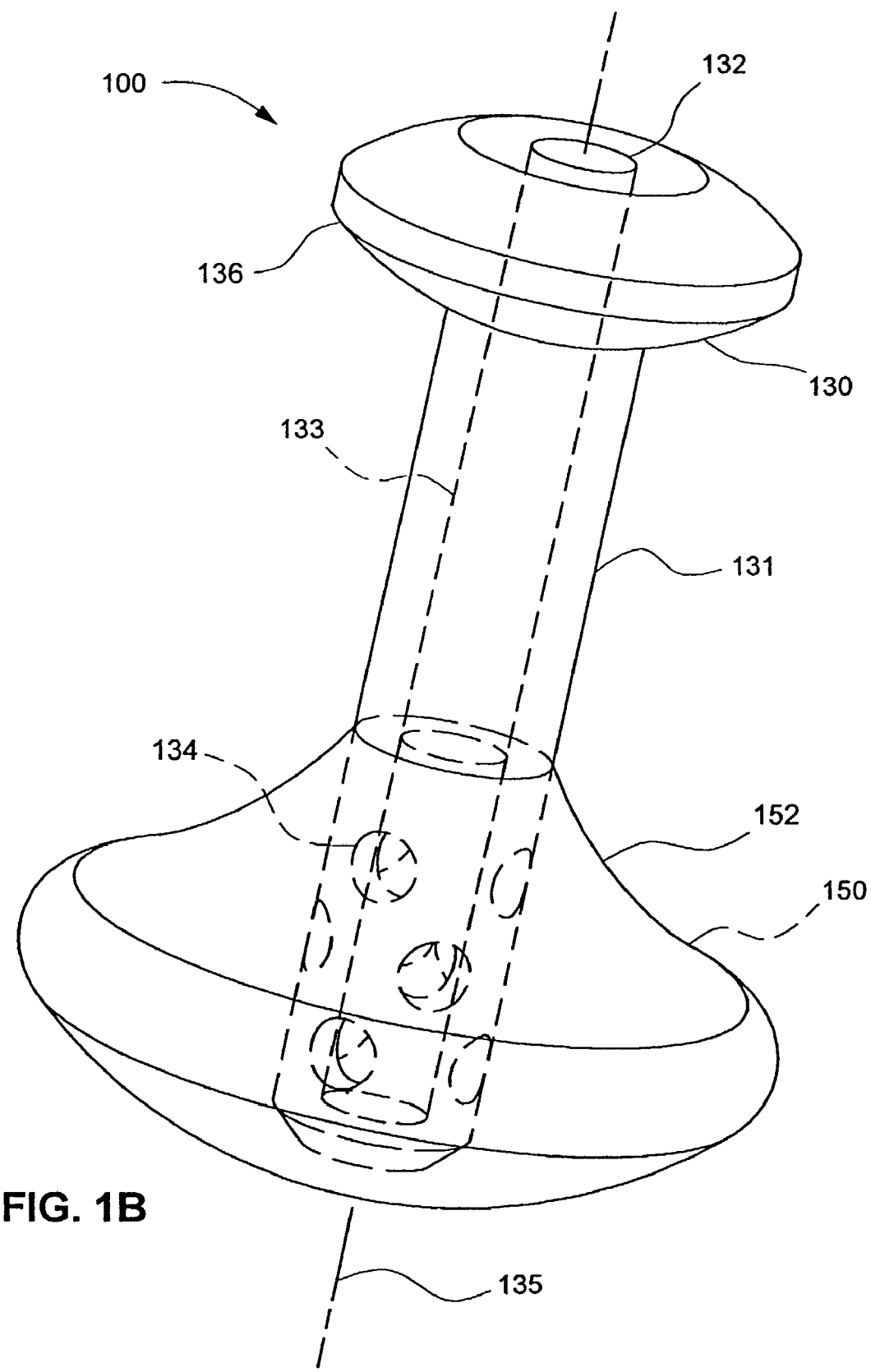
FIG. 1B is a perspective view showing a first preferred embodiment of the present invention as a bone fastener to include the preformed element depicted in FIG. 1A and an in-situ formed anchor.
Figure 1C:
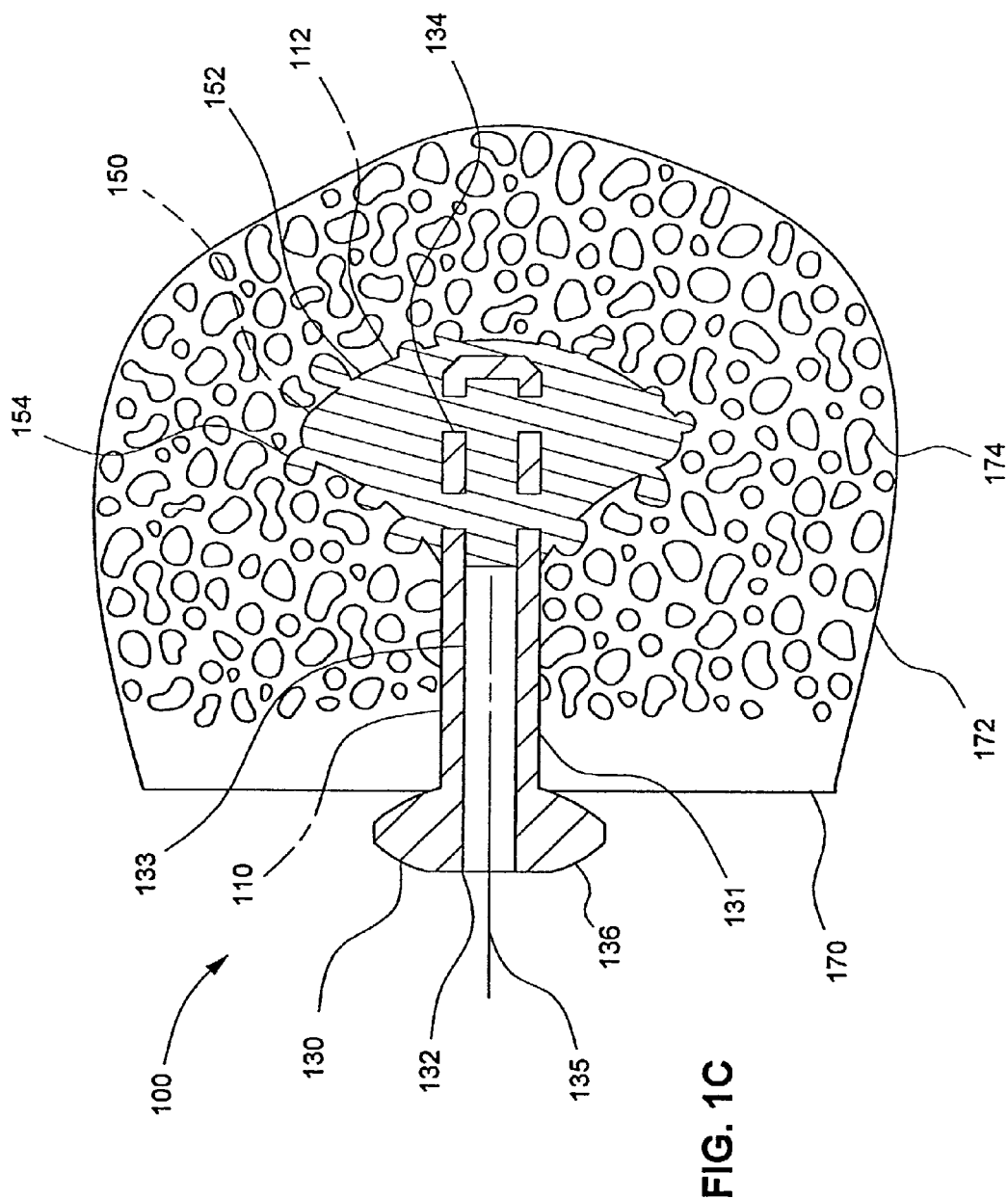
FIG. 1C is an in-situ sectional view in bone depicting the bone fastener of FIG. 1B.

Referring now to FIG. 1A, a perspective view of preformed element 130 includes shank 131, longitudinal axis 135, and head 136. Proximal aperture 132, passage 133, and distal apertures 134 are adapted for the flow of an in-situ hardenable material. Referring now to FIG. 1B, bone fastener 100 represents a first preferred embodiment to include preformed element 130 and an in-situ formed anchor 152. FIG. 1C shows a detailed in-situ sectional view of bone fastener 100 attached to bone 170. Bone 170 is comprised of cortical bone 171 and cancellous bone 172. Surgically created pilot hole 110 is sized to receive and support preformed element 130. Bone cavity 112 has been formed to a specific shape and size, based in part, on anatomical considerations and desired biomechanical performance. Using a preferred method, an in-situ formed anchor 152 is molded within bone cavity 112 from an in-situ hardenable material 150 in an interlocking manner with preformed element 130. That is, in-situ formed anchor 152 is molded within bone cavity 112, throughout outlet apertures 134, and within passage 133 in an inter-locking manner. In-situ formed anchor 152 also extends beyond bone cavity 112 into surrounding bone pores 174 to form anchor-bone interlocks 154. Continuing to refer to FIG. 1C, advantages of in-situ formed anchor 152 include formation of a broad foundation for implant fixation, further supported by anchor-bone interlocks 154.

A preformed element can be manufactured from suitably rigid implant materials to include metals, polymers, ceramics, and composites. Specific examples of metals include titanium, titanium alloy, stainless steel, and Nitinol (TiNi). Considering polymers, ceramics, and composites, the preformed element can be made from a resorbable or non-resorbable material. Examples of established resorbable polymers include copolymers derived from glycolide and lactide that resorb in-vivo by hydrolysis to lactic and glycolic acids, which are then metabolized by the body. Examples of established ceramics include ziconia, alumina, and hydroxylapetite.

An in-situ formed-anchor can be molded from numerous injectable biomaterials capable of hardening or curing to a structural material following implantation. The following discussion provides examples, including preferred in-situ hardenable materials; however, the present invention should not be limited to these examples.

Potential in-situ hardenable materials include polymethylmethacrylate-based bone cements. Although these injectable bone cements have been used effectively for many decades, there continues to be concerns regarding high exothermic curing temperatures and potentially toxic fumes produced during curing.

Other in-situ hardenable materials appropriate for an in-situ formed anchor includes those said to have structural properties appropriate for load-bearing orthopaedic implants. For example, U.S. Pat. No. 5,990,194 to Dunn et. al. discloses biodegradable thermoplastic and thermosetting polymers for use in providing for syringeable, in-situ forming, solid biodegradable implants.

U.S. Pat. No. 6,264,659 to Ross et. al. describes a thermoplastic implant material, that is heated to a predetermined high temperature for injection from a needle. After injection, the thermoplastic material is cooled by the body temperature for setting of the thermoplastic material to a non-flowing state. The preferred thermoplastic material is said to be gutta-percha or gutta-percha compound.

Preferred in-situ hardenable materials include synthetic bone substitutes. For example, resorbable and injectable calcium phosphates, such as the material offered by Synthes-Stratec, Inc. under the Norian Skeletal Repair System™ brand name. An example of a non-resorbable bone substitute is an injectable terpolymer resin with combeite glass-ceramic reinforcing particles, such as the material offered by Orthovita, Inc. under the Cortoss™ brand name. Cortoss™ is said to have strength comparable to human cortical bone.

Those skilled in the art can envision numerous combinations of materials appropriate for various applications. For example, considering bone fastener 100, shown in FIGS. 1B and 1C, preformed element 130 can be machined from a titanium 6-Al-4V alloy and in-situ formed anchor 152 can be molded in-situ from a synthetic bone substitute, such as Cortoss™.

Figure 2A:
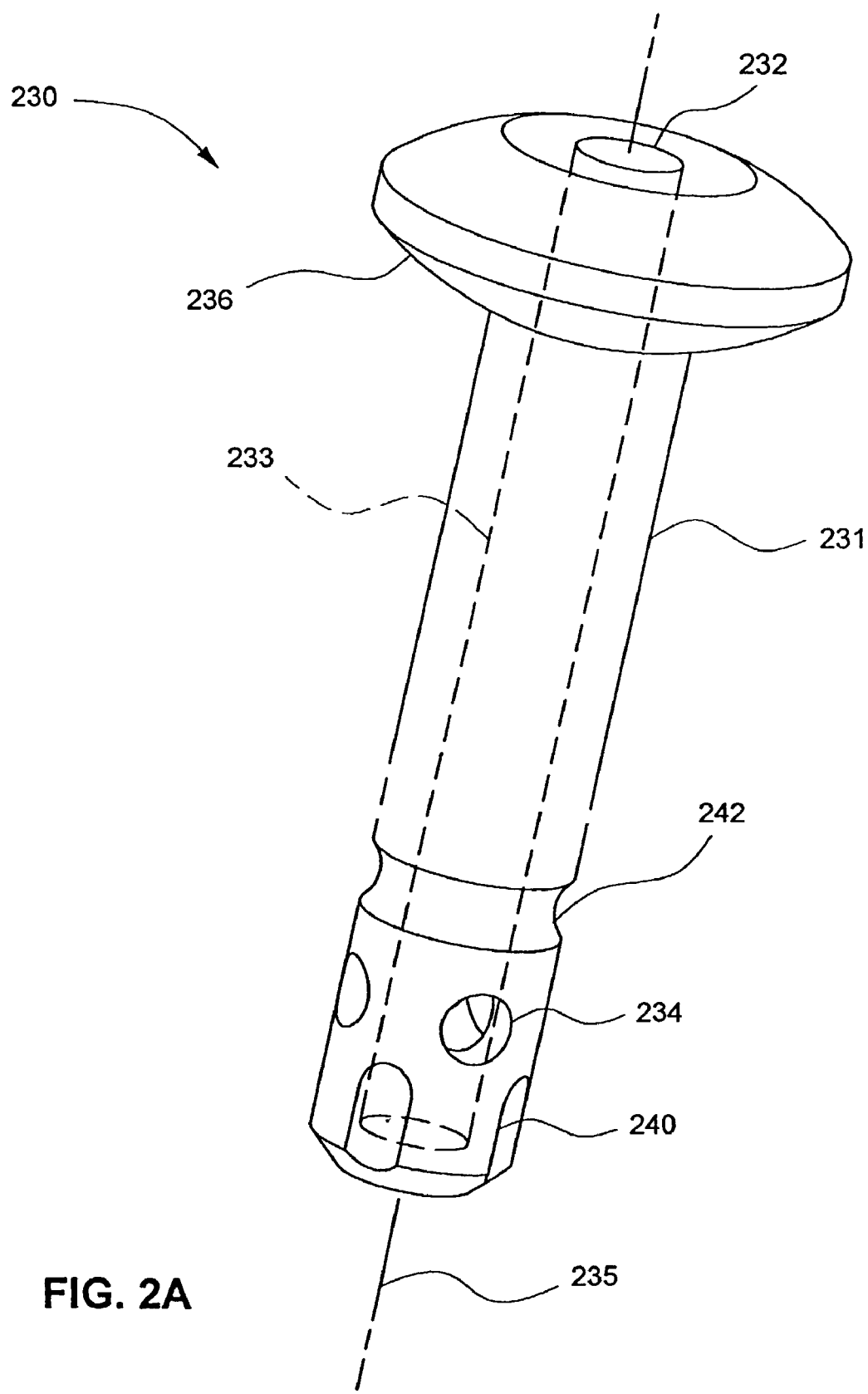
FIG. 2A is a perspective view of a preformed element.
Figure 2B:
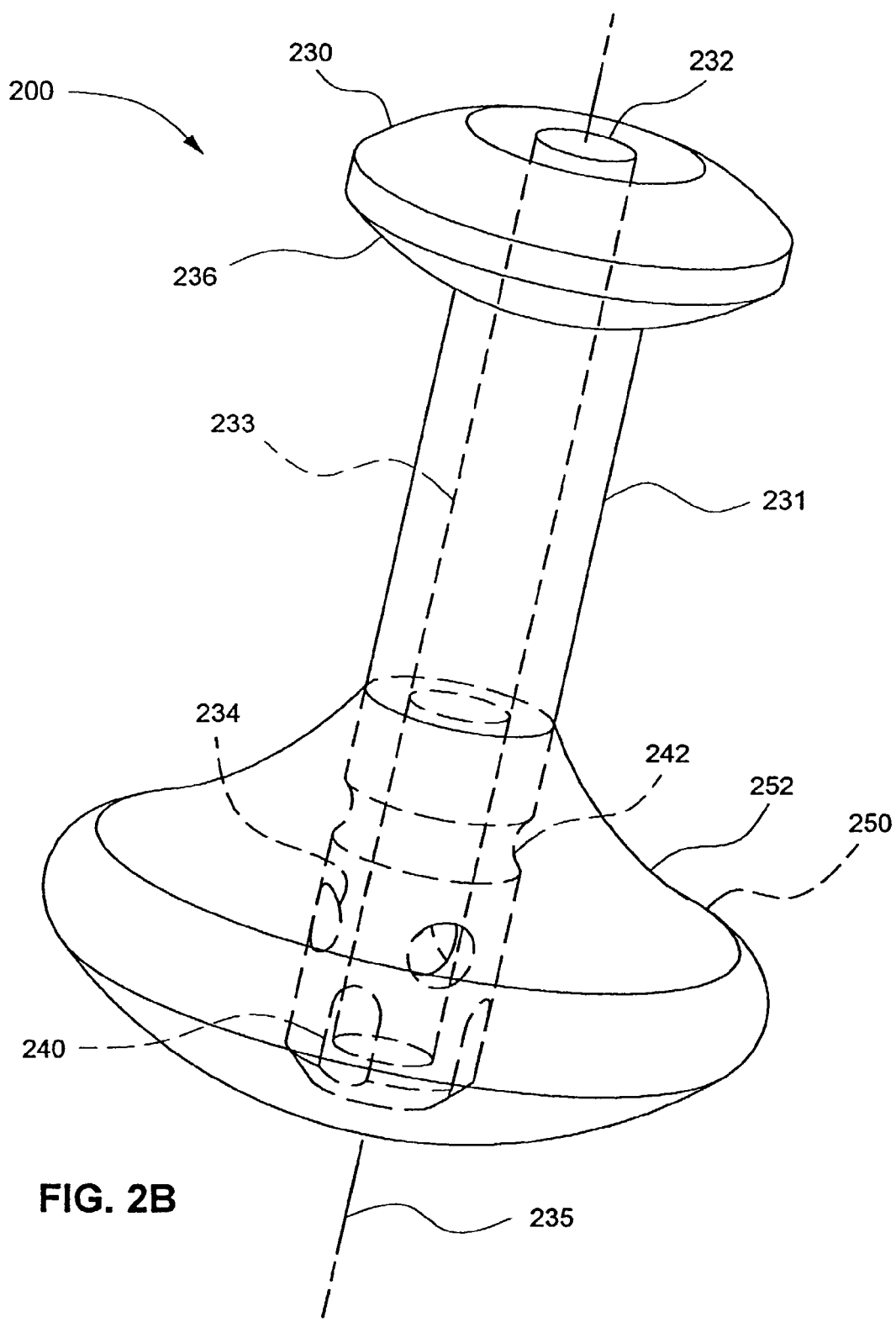
FIG. 2B is a perspective view showing a second preferred embodiment of the present invention as a bone fastener to include the preformed element depicted in FIG. 2A and an in-situ formed anchor.

Relating to the present invention, the preformed element has structures and voids to interlock with an in-situ formed anchor. Structures and voids on a relatively small scale can be considered a surface treatment to include porous coatings or roughened surfaces. On a larger scale, structures include, but are not limited to, flanges, serration, and screw thread. Comparably sized voids include, but are not limited to, holes, slots, grooves, flutes, and dimples. For example, referring now to FIG. 2A, a preformed element 230 is comprised of shank 231, longitudinal axis 235, and head 236. In addition, preformed element 230 has voids adapted for the flow of an in-situ hardenable material to include proximal aperture 232, passage 233, distal apertures 234, longitudinal flutes 240, and transverse groove 242. Referring now to FIG. 2B, bone fastener 200 represents a second preferred embodiment of the present invention. Preformed element 230 is shown interlocking with in-situ formed anchor 252 as a result of in-situ hardenable material 250 molded external to shank 231, throughout distal apertures 234, and partially within passage 233. In-situ formed anchor 252 also interlocks with longitudinal flute 240 in a manner conducive to the transfer of torsional load. Similarly, in-situ formed anchor 252 interlocks with transverse groove 242 in a manner conducive to the transfer of axial load.

Figure 3:
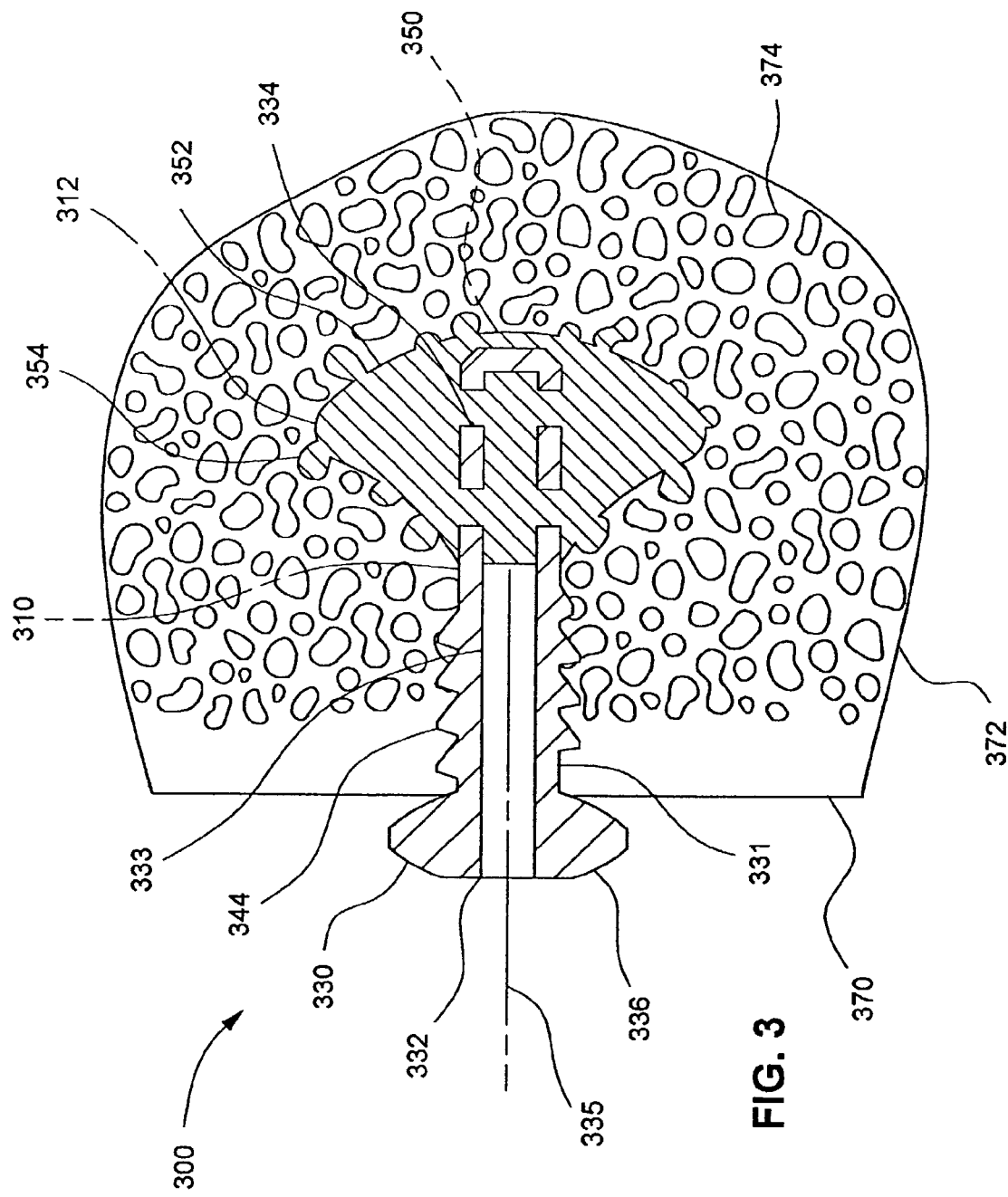
FIG. 3 is an in-situ sectional view in bone showing a third preferred embodiment of the present invention adapted as a bone fastener to include a screw thread adjacent to an in-situ formed anchor.

Orthopaedic fixation using an in-situ formed anchor can be used in conjunction with conventional bone fixation mechanisms, such as a screw thread. For example, FIG. 3 shows an in-situ sectional view of a third preferred embodiment of the present invention, bone fastener 300. Bone fastener 300 is comprised of preformed element 330 and in-situ formed anchor 352. Preformed element 330 is comprised of shank 331, longitudinal axis 335, and head 336. Similar to previous embodiments, proximal aperture 332, passage 333, and distal apertures 334 are adapted for the flow of in-situ hardenable material 350. In general, better screw thread purchase is obtainable in cortical bone 371, as compared to cancellous bone 372. Accordingly, screw thread 344 is adjacent to head 336 for purchase in cortical bone 371, whereas in-situ formed anchor 352 is formed within bone cavity 312 in cancellous bone 372. Anchor-bone interlock 354 and the large size of in-situ formed anchor 352 in comparison to pilot hole 310 diameter is advantageous in preventing rotation and coupled axial translation of preformed element 330 that can be associated with a phenomena called "screw back-out".

The present invention can be adapted for use with existing bone screws serving as a preformed element. In this instance, a screw thread interlocks with an in-situ formed anchor. Accordingly, the present invention can be readily integrated into existing implant systems. Bone screws with in-situ formed anchors can be used as part of a planned procedure or part of a salvage procedure when the surgeon experiences unanticipated stripping of bone during tightening of a bone screw. The following description and drawings consider the use of cannulated bone screws and non-cannulated bone screws as preformed elements.

Figure 4:
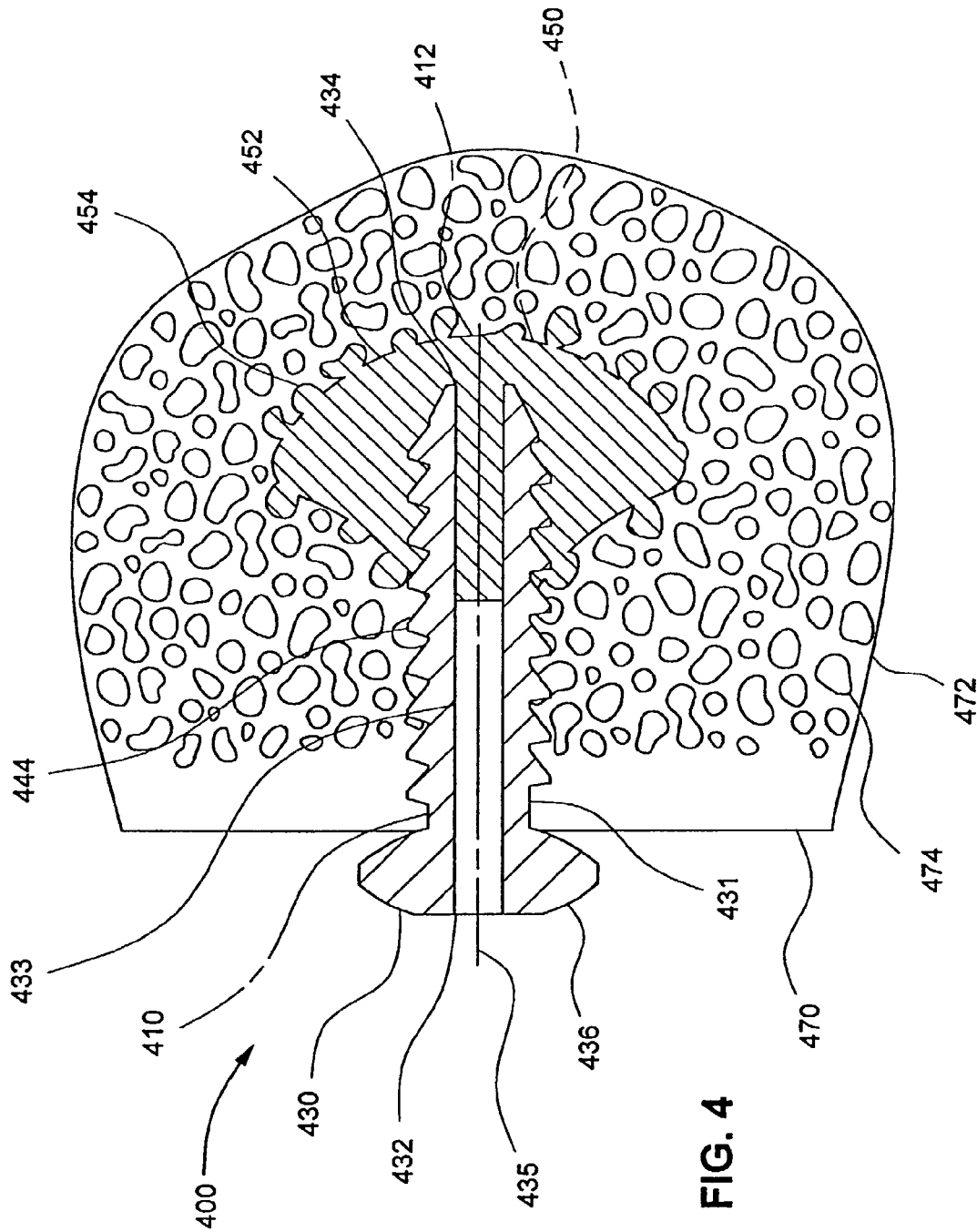
FIG. 4 is an in-situ sectional view in bone showing a fourth preferred embodiment of the present invention adapted as a bone fastener to include a cannulated bone screw and an in-situ formed anchor.

Referring now to FIG. 4, an in-situ sectional view of a fourth preferred embodiment of the present invention, bone fastener 400. Bone fastener 400 is comprised of preformed element 430 and in-situ formed anchor 452. In the basic form of cannulated bone screw, preformed element 430 is comprised of shank 431, proximal aperture 432, passage 433, distal aperture 434, longitudinal axis 435, head 436, and screw thread 444. Head 436 also has a conventional means (not shown) for releasably connecting with a surgical instrument capable of transmitting torsion, such as, a screwdriver. Bone 470 is comprised of cortical bone 471, cancellous bone 472, and bone pores 474. Pilot hole 410 is typically smaller than the major diameter of thread 444 and preformed element 430 is threaded into pilot hole 410 and positioned within bone cavity 412. Using a preferred method, in-situ formed anchor 452 can be created by injection of in-situ hardenable material 450 through proximal aperture 432, passage 433, and distal aperture 434. Continuing to refer to FIG. 4, in-situ formed anchor 452 has been formed in an interlocking manner with screw thread 444. Further, in-situ formed anchor 452 extends outward to form anchor-bone interlocks 454. Since the addition of transverse apertures to a screw thread can substantially weaken an implant, preformed element 430 has a single distal aperture 434 co-axial with passage 433 and longitudinal axis 435. However, the distal aperture 434 is positioned advantageously within bone cavity 412 to allow for a retrograde flow of an in-situ hardenable material 450 within bone cavity 412.

Figure 5:
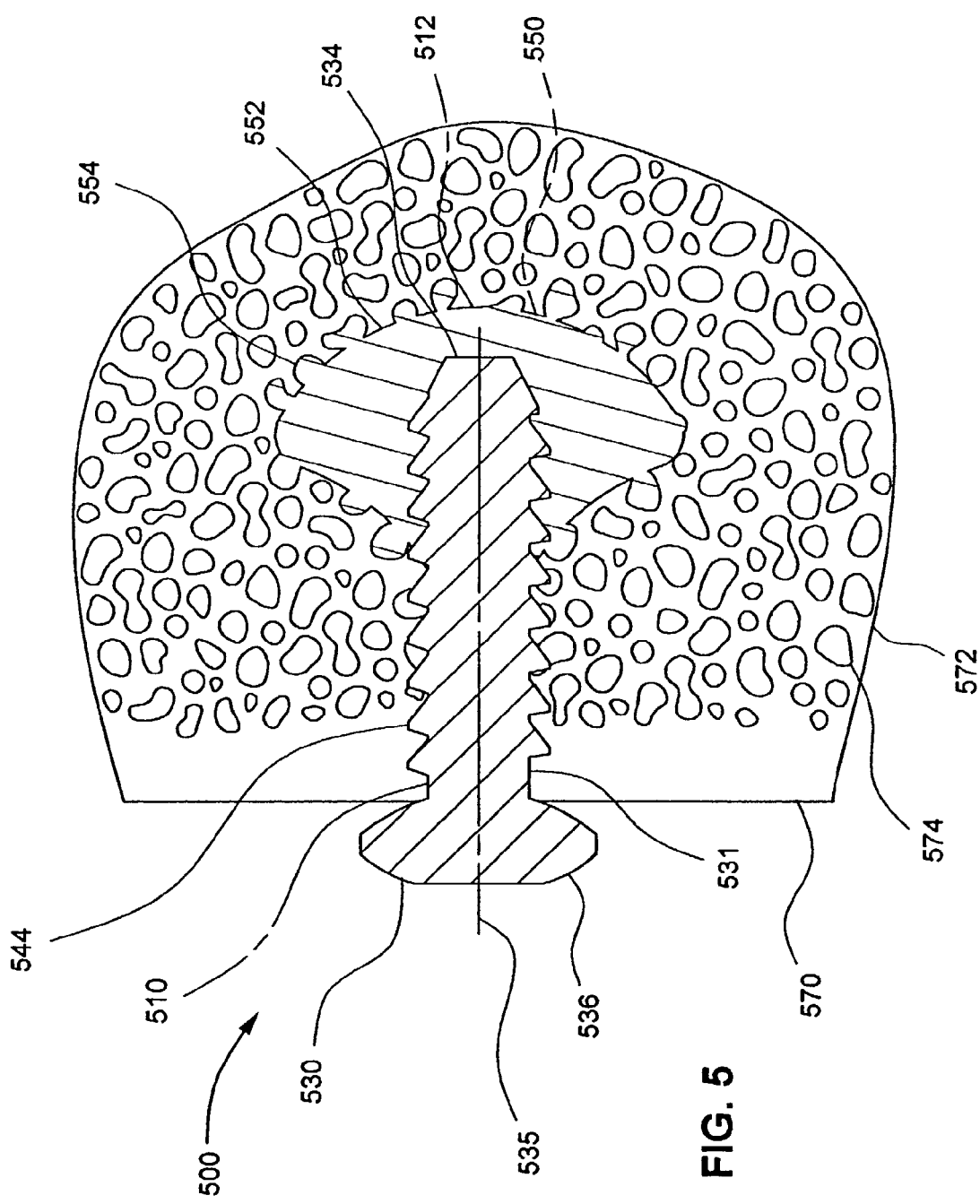
FIG. 5 is an in-situ sectional view in bone showing a fifth embodiment of the present invention adapted as a bone fastener to include a bone screw and an in-situ formed anchor.

The present invention can also be adapted to non-cannulated bone screws, that is bone screws that do not have an internal passage or apertures for flow of an in-situ hardenable material. FIG. 5 shows an in-situ sectional view of a fifth preferred embodiment of the present invention, bone fastener 500. Bone fastener 500 is comprised of preformed element 530 and in-situ formed anchor 552. In the basic form of bone screw, preformed element 530 is comprised of shank 531, longitudinal axis 535, head 536, and screw thread 544. Head 536 also has a conventional means (not shown) for releasably connecting with a surgical instrument capable of transmitting torsion, such as, a screwdriver. FIG. 5 also shows bone 570, comprised of cortical bone 571 and cancellous bone 572. Using a preferred method, an in-situ hardenable material 550 can be injected into a bone cavity 512 prior to implanting preformed element 530. Upon embedding preformed element 530 into in-situ hardenable material 550, in-situ hardenable material 550 hardens to form an in-situ formed anchor 552 in an interlocking manner with the screw thread 544. In-situ formed anchor 552 also extends into the bone pores 574 to form anchor-bone interlocks 554.

All preceding preferred embodiments, and variations thereof, can be considered versatile bone fasteners that can used as a stand-alone system for fracture repair, or adapted to work with numerous other implant components including, but not limited to, bone plates. The remaining preferred embodiments are examples of the present invention adapted to additional orthopaedic implant systems and related applications.

The proximal end of the femur, particularly the neck region, is susceptible to osteoporosis related fractures. These types of fractures are often treated with a bone screw system in the head of the femur. More specifically, the bone screw used is a stand-alone lag screw, or a sliding lag screw as part of a compression hip screw system. The compression hip screw system also has bone plate component. Screw systems are designed to reduce the fracture and support the neck of the femur during healing. Fixation using lag screws, or a compression hip screw system are preferable to the considerably more invasive total hip arthroplasty. However, the success of these devices relies on adequate screw purchase within the femoral head's cancellous bone. It is possible to strip the bone structure when tightening a relatively large lag screw, which can lead to a conversion of the surgery to total hip arthroplasty.

Figure 6:
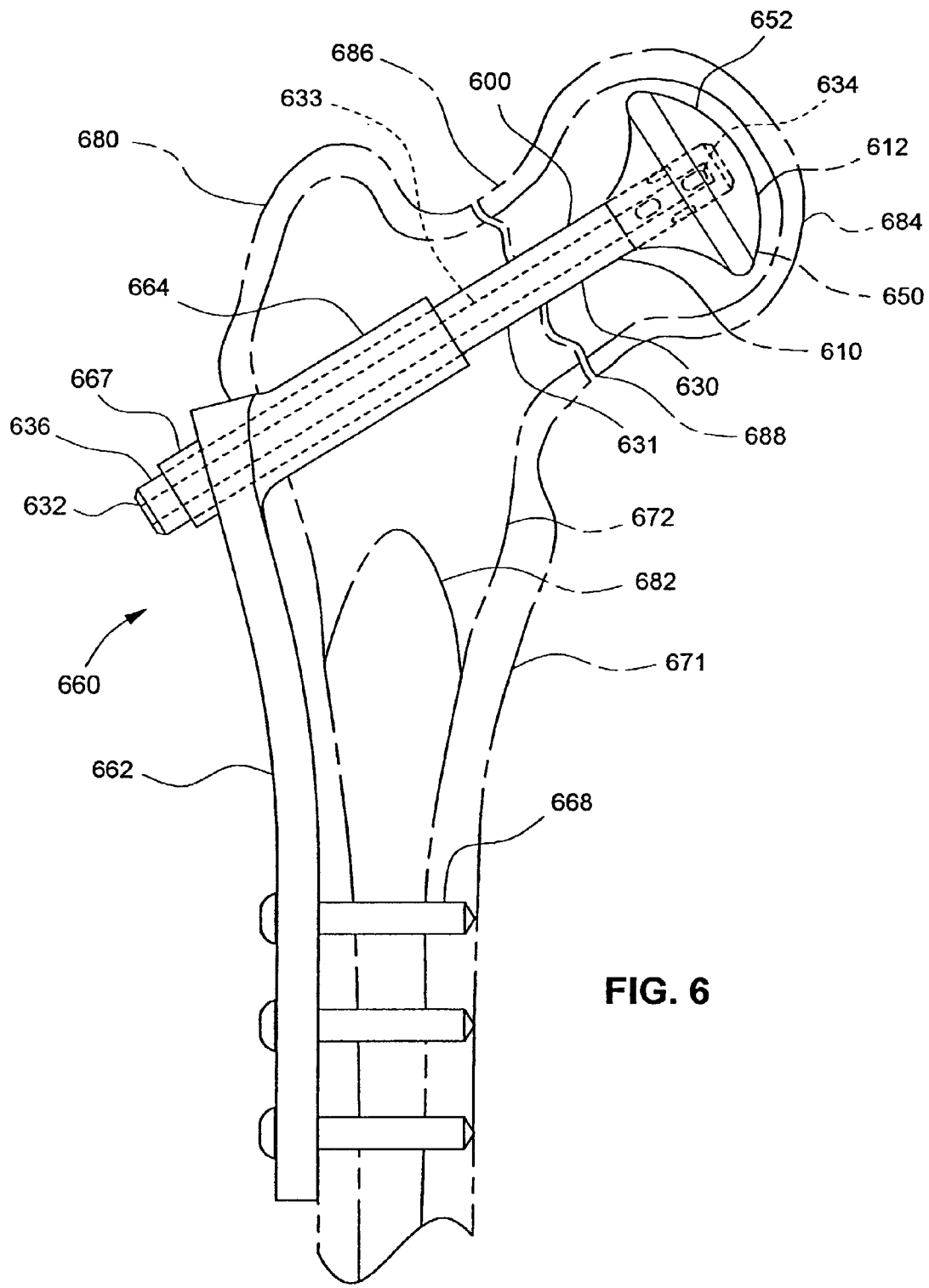
FIG. 6 is a partial sectional view showing a sixth preferred embodiment of the present invention adapted as compression hip system to treat fractures in the neck of a human femur.

Referring now to FIG. 6, a compression hip system 660 represents a sixth preferred embodiment of the present invention. Femur 680 has the following anatomical structures: medullary canal 682, head 684, and neck 686. In addition, femur 680 has regions of cortical bone 671 and cancellous bone 672. Compression hip system 660 has been adapted for fixation of neck fracture 688. Those skilled in the art will appreciate the methods and components common to conventional compression hip screw systems, to include plate 662, barrel 664, and plate screws 668. Compression hip system 660 further includes a sliding lag fastener 600 to include a preformed element 630 and an in-situ formed anchor 652. Sliding lag fastener 600 is comprised of a shank 631, inlet aperture 632, passage 633, outlet aperture 634, and threaded end 636. Femur 680 is prepared with a pilot hole 610 and bone cavity 612. Using a preferred method, in-situ hardened anchor 652 can be formed by injecting an in-situ hardenable material 650 into a surgically created bone cavity 612 in an interlocking manner with preformed element 630. Nut 667 can be engaged on threaded end 636 to reduce fracture 688 using known surgical techniques. Although not shown, shank 631 is typically a non-circular cross-section to prevent rotation within barrel 664. Considering existing compression hip screw systems, a sliding lag fastener 600, and variations thereof, can be used as an alternative to a sliding lag screw, or as part of a salvage procedure when the surgeon experiences unanticipated stripping of bone during tightening of a sliding lag screw.

Figure 7:
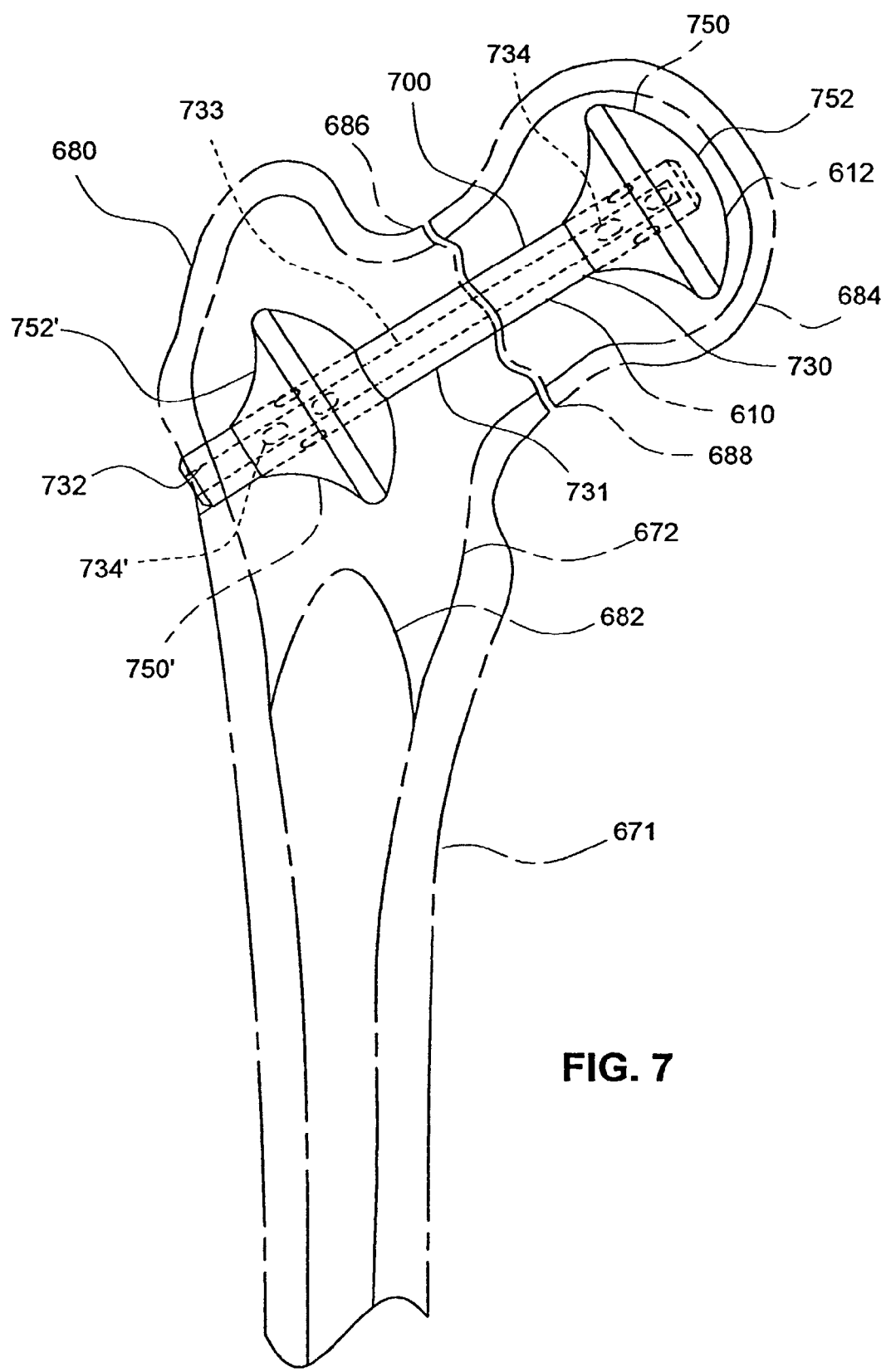
FIG. 7 is a partial sectional view showing a seventh preferred embodiment of the present invention adapted as compression hip system with multiple in-situ formed anchors.

Referring now to FIG. 7, compression hip fastener 700 represents a seventh preferred embodiment of the present invention. Similar to compression hip system 660, compression hip fastener 700 has been adapted for fixation of fracture 688. The femur 680 depicted in FIG. 6 is also shown in FIG. 7. Compression hip fastener 700 has preformed element 730 interlocking with multiple in-situ formed anchors 752, 752'. Proximal aperture 732, passage 733, and distal apertures 734, 734' are adapted for flow of an in-situ hardenable material 750 to facilitate interlocking preformed element 730 to in-situ formed anchors 752, 752'. An advantage of compression hip fastener 700 is the potential for less invasive surgery, as the procedure can be conducted through a single guide tube with a diameter capable of passing preformed element 730. Bone fasteners, similar in configuration to compression hip fastener 700, can be used for minimally invasive fracture repair surgery throughout the skeletal system.

Intramedullary nails are often used to stabilize a fracture of the diaphysis (mid-shaft) of long bones, such as, the femur. In the case of a femur, intramedullary nails are placed through the greater trochar and into the intramedullary canal. The tip of the intramedullary nail terminates at the distal end, near the epicondyles of the knee joint. Most intramedullary nails have transverse holes at the proximal end and distal end for interlocking screws that secure the intramedullary nail to the femur. Because the proximal end is near the incision site, the surgeon can use the proximal end of the intramedullary nail as a foundation for a temporary drill guide fixture to drill through holes for the proximal interlocking screws. Targeting the interlocking screws at the distal end of the nail is inherently difficult because the nail is embedded in bone a considerable distance from the surgical opening used to insert the nail. There have been attempts to use a second drill guide fixture for targeting the distal interlocking screws, also using the easily accessed proximal end of the nail as a temporary foundation and reference point. However, because of the significant distances involved, these fixtures have not been appropriately accurate. Therefore, a common approach for targeting the distal interlocking screws involves a time-consuming freehand technique of placing guide pins or drill guides with the assistance of a fluoroscope. More elaborate image guided surgery systems and other targeting systems are being developed; however, placing the distal interlocking screws remains one of the more difficult and time-consuming aspects of intramedullary nailing. The in-situ formed anchor of the present invention has the potential to serve as an alternative to interlocking screws at the distal end of an intramedullary nail.

Figure 8:
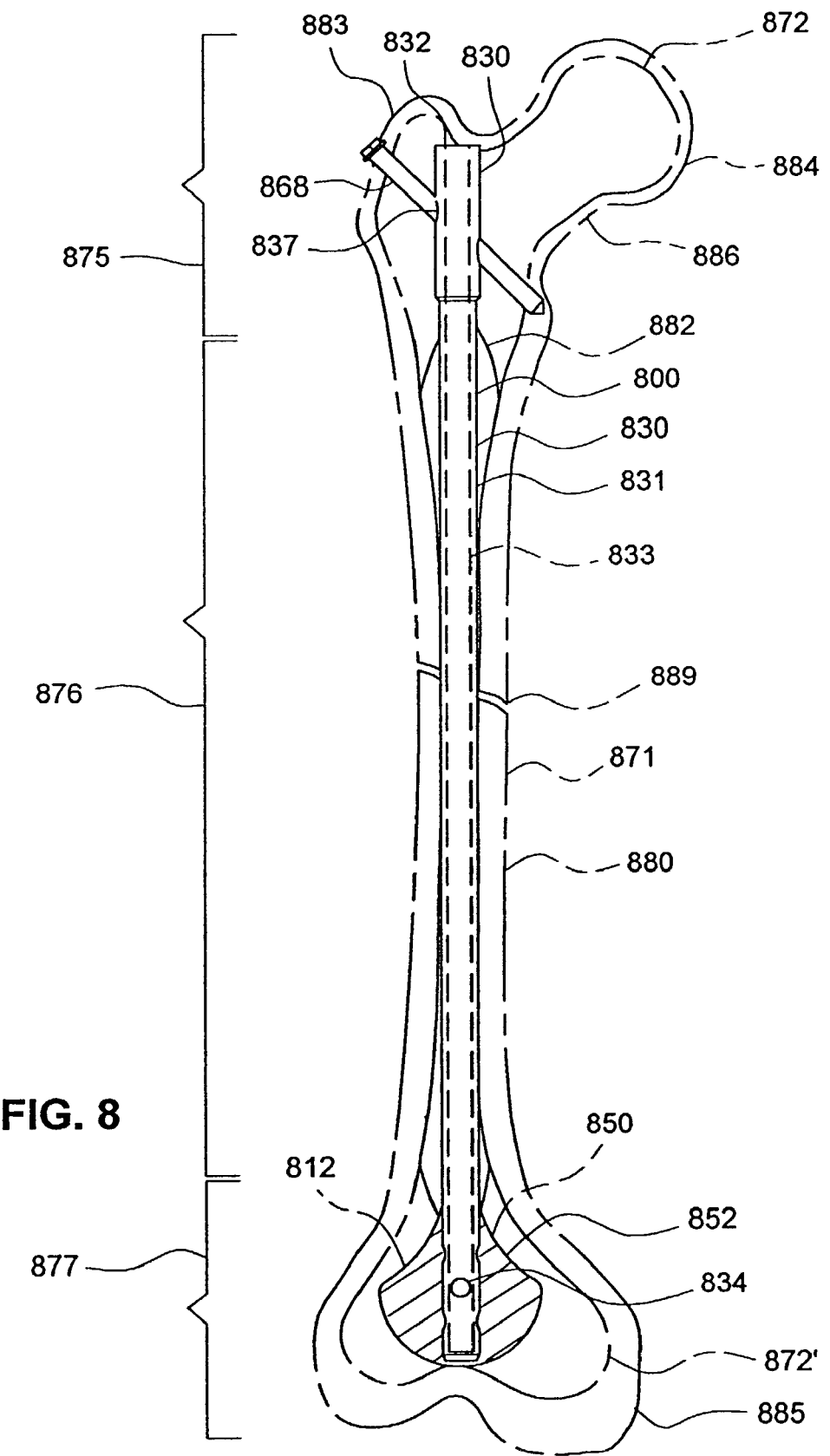
FIG. 8 is a partial sectional view showing a eighth preferred embodiment of the present invention adapted for use as an intramedullary nail to treat fractures of a human femur.

Referring now to FIG. 8, a partial sectional view is shown to include a femur 880 and intramedullary nail system 800, the latter representing an eighth preferred embodiment of the present invention. Intramedullary nail system 800 is comprised of intramedullary nail 830, interlocking screw 868, and in-situ formed anchor 852. Intramedullary nail 830 is comprised of nail body 831, proximal aperture 832, passage 833, distal apertures 834, proximal section 836, and oblique hole 837. Femur 880 is divided into three anatomical regions, proximal epiphysis 875, diaphysis 876, and distal epiphysis 877. Femur 880 anatomical structures include medullary canal 882, greater trochanter 883, head 884, epicondyles 885, and neck 886. Proximal epiphysis 875 and distal epiphysis 877 are comprised of cortical bone 871 and cancellous bone 872, 872'. Femur 880 is also shown with fracture 889 of the diaphysis 876. Using known surgical techniques, the femur 880 is prepared for the intramedullary nail system 800, to include pilot hole 810 extending from greater trochanter 883 to distal epiphysis 877 cancellous bone 872'. In addition, bone cavity 812 is created in distal epiphysis 877 cancellous bone 872'. Using a preferred method, in-situ formed anchor 852 is molded within the bone cavity 812 from in-situ hardenable material 850 in an interlocking manner with distal apertures 834, passage 833, and surrounding cancellous bone 872'. Compared to conventional distal interlocking screws, an in-situ formed anchor is advantageous because only a proximal incision is necessary and extensive fluoroscope imaging and elaborate targeting systems are not required.

Suture anchors and interference screws are often used for soft tissue repair and reconstruction of damaged ligament and tendons in the shoulder, knee, wrist, hand, and ankle. Suture anchors can also be used to repair other soft tissues in the musculoskeletal system, such as a labral tear in the shoulder joint. Suture anchors, in particular, are subjected to forces that can lead to pullout, a problem that is exasperated by attachment to osteoporotic cancellous bone. Minimally invasive arthroscopic surgery has been increasing used in orthopaedics, especially for the aforementioned soft tissue repair. The surgical instruments used in arthroscopic surgery, to include tubular guides, are typically 3 mm to 4 mm in diameter. In general, implants that can be inserted through smaller diameter tubular guides are desirable, because this is less invasive and intraoperative viewing is improved.

Figure 9A:
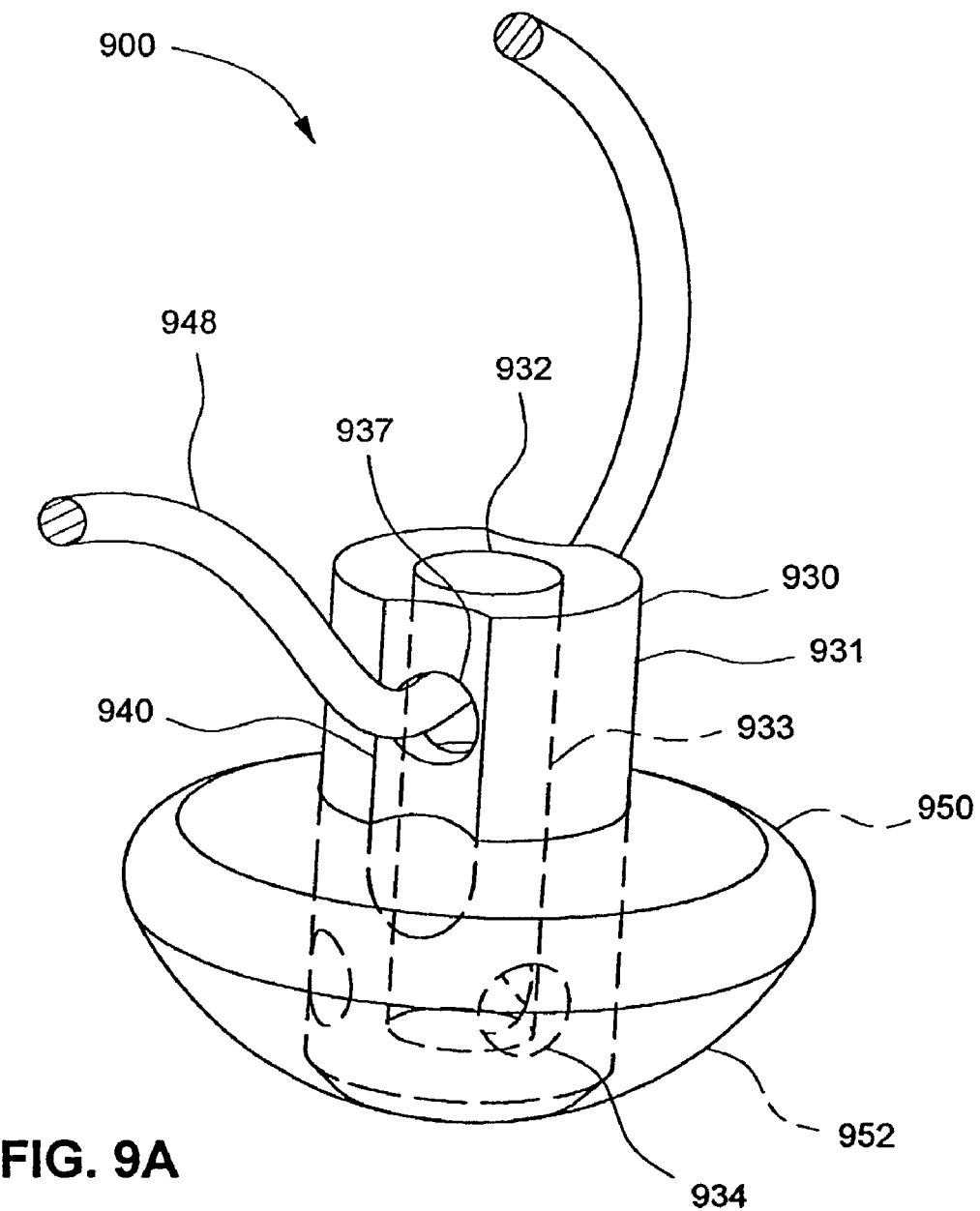
FIG. 9A is a perspective view of a ninth preferred embodiment of the present invention adapted for use as a suture anchor to include a preformed element and an in-situ formed anchor.
Figure 9B:
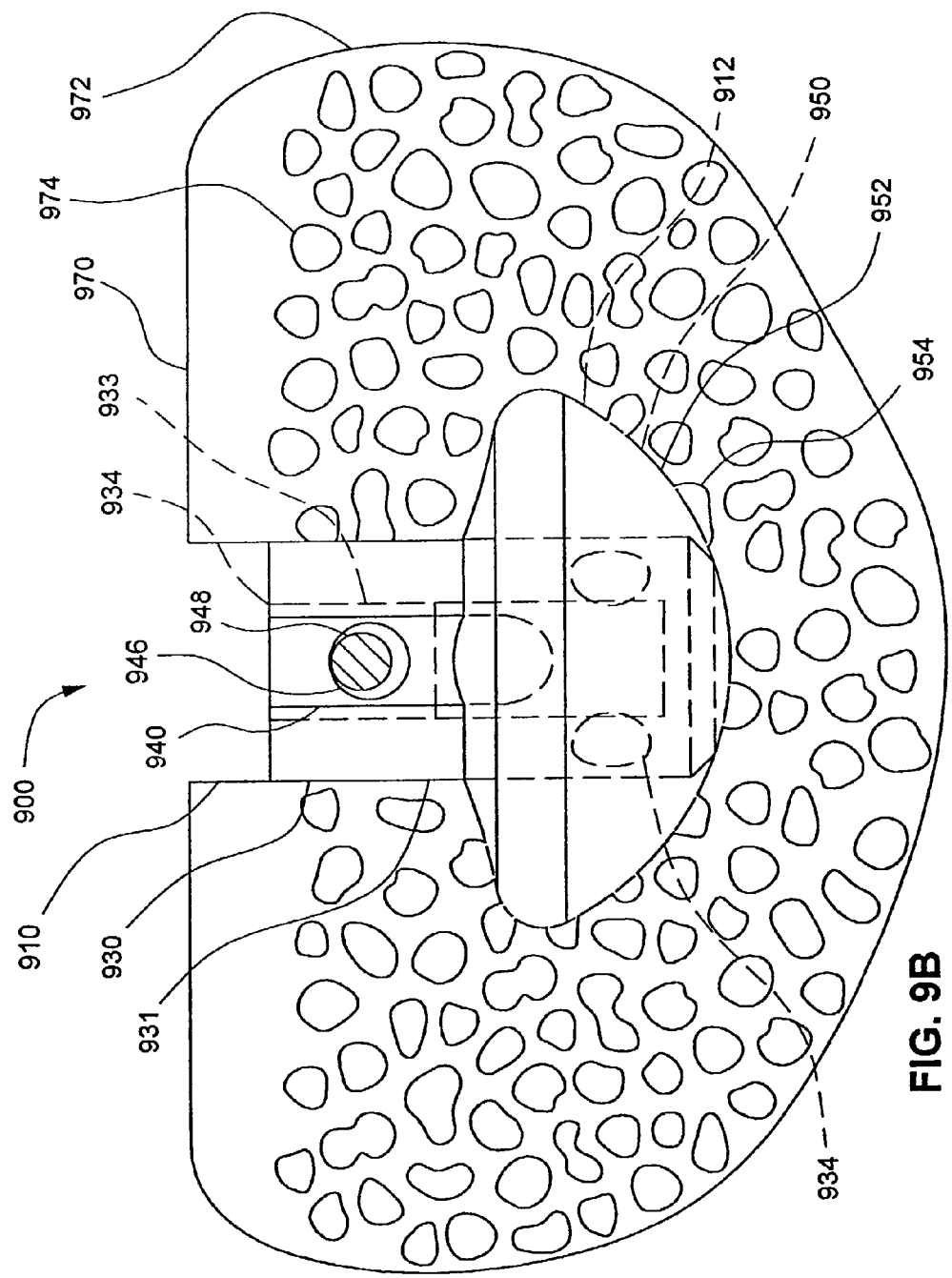
FIG. 9B is an in-situ partial sectional view in bone of the suture anchor depicted in FIG. 9A.

Referring now to FIG. 9A, suture anchor 900 is shown, representing a ninth preferred embodiment of the present invention. Suture anchor 900 is comprised of a preformed element 930, in-situ formed anchor 952, and suture 948. Preformed element 930 has inlet aperture 932, distal apertures 934 interconnected by passage 933. Suture 948 is threaded through eyelet 937. FIG. 9B shows an in-situ partial sectional view of suture anchor 900 in bone 970. Bone 970 is comprised of cortical bone 971 and cancellous bone 972. Preformed element 930 is shown suitably positioned within surgically prepared pilot hole 910 and bone cavity 912. Longitudinal channel 940 serves as a relief for passing suture 948 out of pilot hole 910. In addition, longitudinal channel 940 can serve as a vent for constituents, such as blood, to flow out of bone cavity 912. Using preferred methods, in-situ formed anchor 952 is molded from an in-situ hardenable material 950 within bone cavity 912 in an interlocking manner with distal apertures 934 and passage 933. In addition, anchor-bone interlocks 954 are formed when in-situ hardenable material 950 extends from in-situ formed anchor 952 to fill, or partially fill adjacent cancellous bone pores 974. The large diameter of in-situ formed anchor 952 relative to the diameter of pilot hole 910, results in a suture anchor 900 capable of high pullout resistance. Compared to suture anchors with traditional attachment mechanisms (screw thread, expanding barbs), suture anchor fixation with an in-situ formed anchor is advantageous because the attachment mechanism is injected. Therefore, suture anchors adapted with the present invention are capable of passage through smaller, less invasive, tubular guides, while providing relatively large bone anchors integrally attached to bone.

The following description and drawings pertain to preferred methods associated with orthopaedic implant fixation using an in-situ formed anchor. Discussion topics include preparation of a suitable pilot hole and bone cavity. In general, a preformed element and an in-situ formed anchor are implanted sequentially, the latter molded from an injected in-situ hardenable material. A first preferred method comprises first implanting a preformed element, secondly, injecting an in-situ hardenable material into a bone cavity to form an in-situ formed anchor. A second preferred method comprises an alternate sequence, first injecting an in-situ hardenable material into a bone cavity, secondly, implanting a preformed element to form an in-situ formed anchor. Alternate methods for injecting and removing material from the bone cavity will also be discussed. Although the first preferred embodiment, bone fastener 100 (FIGS. 1B to 1C), is used as a primary example, the following discussion is applicable to all preferred embodiments, except where noted.

A pilot hole and bone cavity are essential aspects of the present invention. Pilot holes are used to position implants and instruments, and in the instance of the present invention, to initiate a bone cavity and ultimately serve as a conduit to the bone cavity. Pilot holes can be created using known techniques and readily available surgical drills and drill bits. Surgical dills can be powered (electric or pneumatic) or manual (e.g., shaft and T-handle).

The term "cavitation device" will refer to devices capable of creating a bone cavity extending from a pilot hole. Generally, a cavitation device can be operated through tubular guides as part of a minimally invasive surgical approach. For example, U.S. Pat. No. 6,066,154 to Reiley et al. discloses an inflatable, balloon-like device for forming a cavity within cancellous bone. The Reiley et al. cavitation device is inserted into the tissue and then inflated to form the cavity by compressing surrounding bone tissue.

Other cavitation devices are adapted to work with a surgical drill. These cavitation devices are said to be capable of creating cavities of various sizes and axisymmetric shapes. For example, U.S. Pat. No. 5,928,239 to Mirza discloses a percutaneous surgical cavitation device adapted for use with a high-speed surgical drill. The Mirza cavitation device comprises an elongated shaft and a separate cutting tip that is connected to one end of the shaft by a freely rotating hinge. A preferred cavitation device and method is described in patent application Ser. No. 09/872,042 to Middleton et. al, which is hereby incorporated by reference. The Middleton cavitation device is comprised of a rotatable shaft interconnected to flexible cutting element. The flexible cutting element has a first shape suitable for minimally invasive passage into tissue, and the flexible cutting element has a means to move toward a second shape suitable for forming a cavity in tissue. Several preferred embodiments can be adapted to either a powered or manual surgical drill.

Figure 10A:
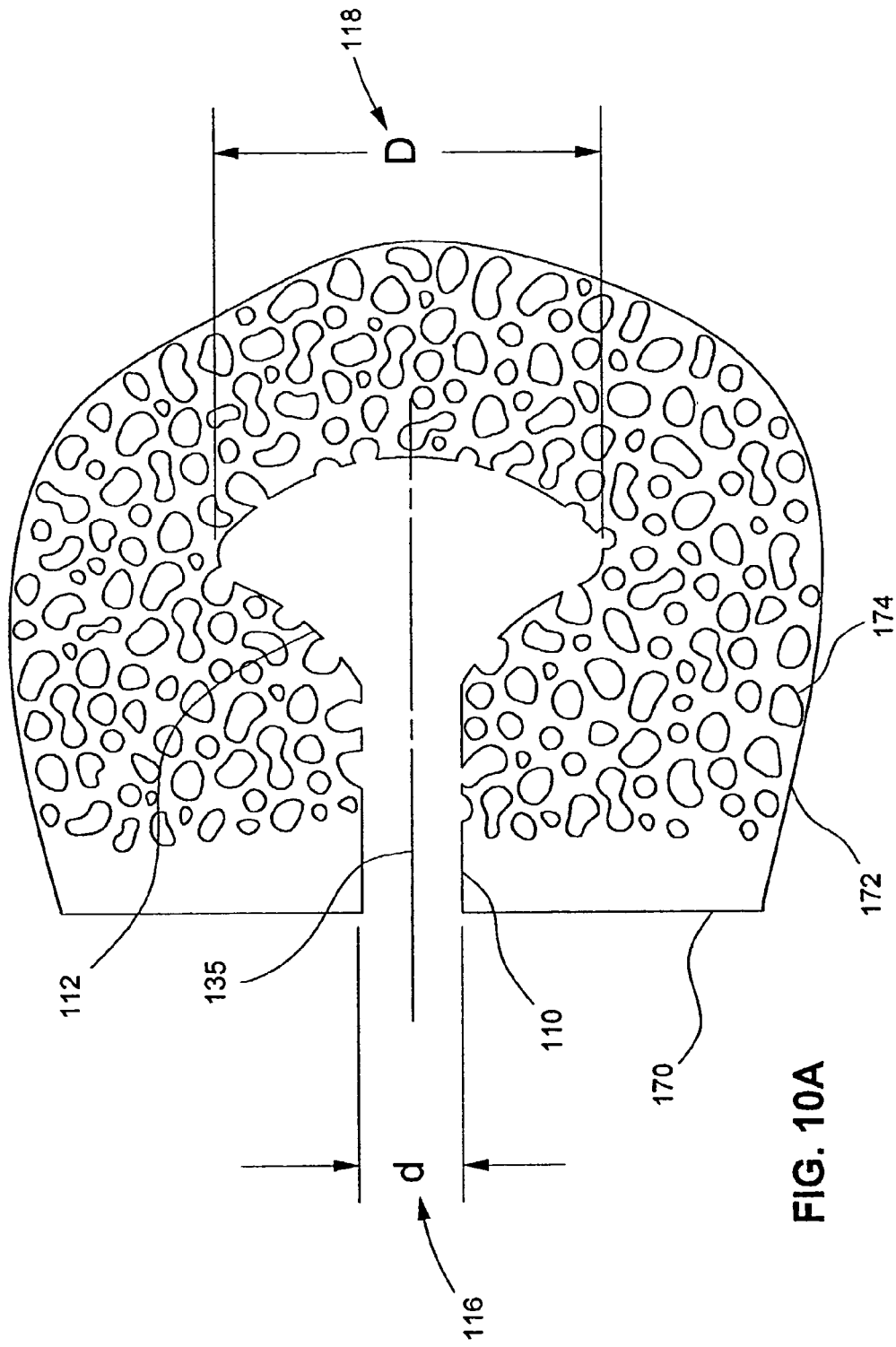

Referring now to FIG. 10A, an in-situ sectional view is shown to include bone 170 consisting of cortical bone 171 and cancellous bone 172. With respect to axis 114, readily available manual or powered surgical drills can be used to form pilot hole 110 with diameter "d" 116. Using a cavitation device, bone cavity 112 is formed with diameter "D" 118. Diameter "D" 118 is substantially larger than diameter "d" 116. Bone cavity 110 is formed to a specific shape and size, based in part on anatomical structures and desired biomechanical performance of the implant. Use of pilot hole 110 also results in the preservation of stronger cortical bone 171.

With respect to cavitation devices adapted for use with surgical drills, attainable bone cavity shapes include cylindrical, hemispherical, or spherical. However, other shapes are possible, as well as interconnecting composite bone cavities. In addition, a bone cavity, or multiple bone cavities can exist along a pilot hole. Additional preparation of the pilot hole and bone cavity can include irrigation and suction of cut bone and the administration of various medicines.

Depending on the nature of the selected in-situ hardenable materials numerous injection devices and supporting devices can be appropriate for delivery. The simplest devices can be in the form of a syringe, or an injection device can be described as an application gun. Some in-situ hardenable materials are comprised of two or more compounds mixed together to form an injectable material that hardens or cures in-situ through a chemical reaction. Mixing can occur in a separate device or an injection device can have a means for storing multiple compounds and mixing them during the injection process. For example, the manual injection device for Orthovita's Cortoss™ includes dual cartridges wherein polymerization is initiated when Cortoss™ is expressed through a "static mix-tip".

Figure 10B:
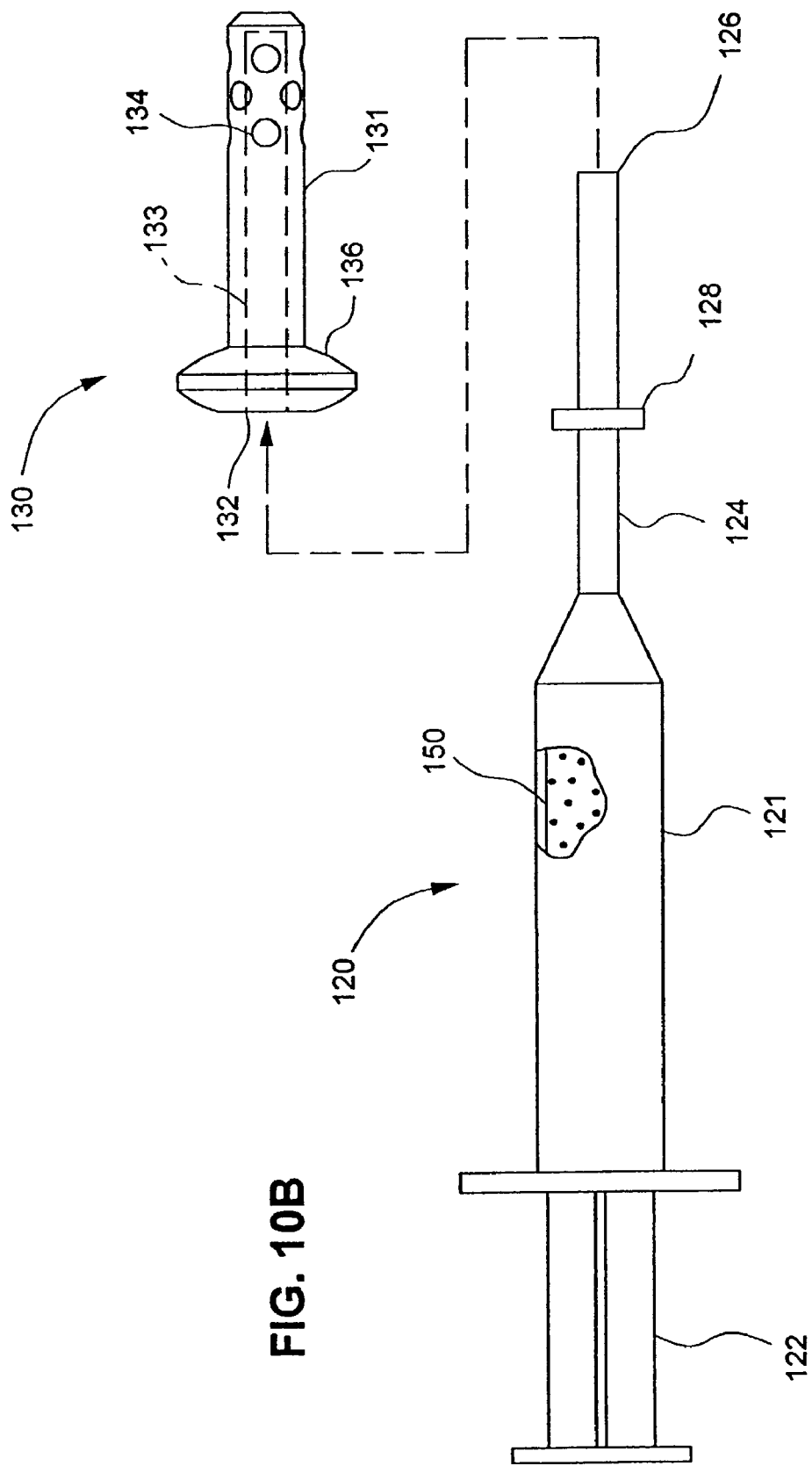
Figure 10C:
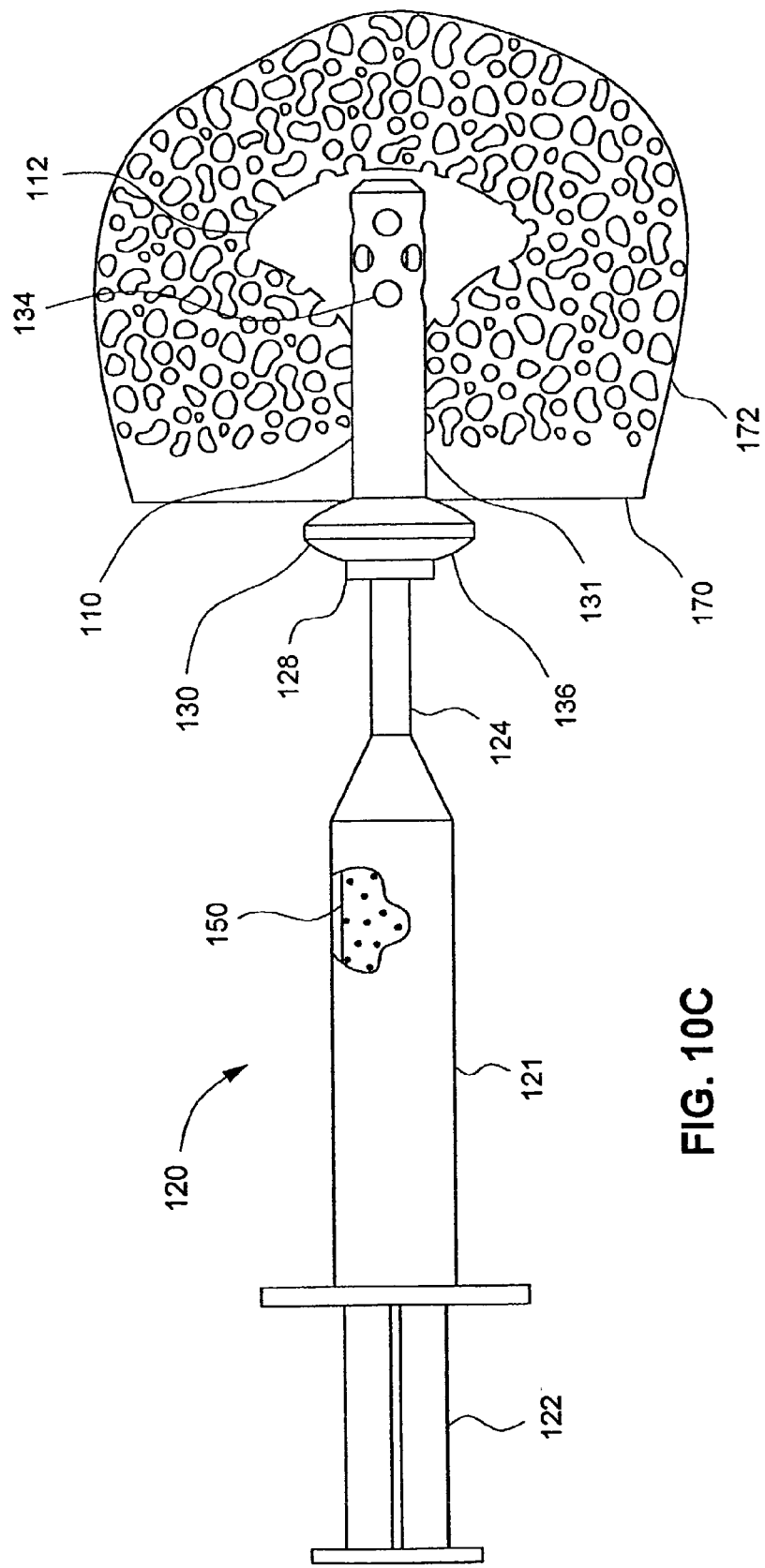

Syringe-like injection devices will be used to further illustrate the preferred methods, but these injection devices do not necessarily pertain to a specific in-situ hardenable material. Referring now to FIG. 10B, injection device 120 is shown in an exploded view with preformed element 130. Injection device 120 includes a reservoir 121, plunger 122, tip 126, and stop 128. Tube 124 is shown as a relatively short section, but variations can be of any suitable length, and further, tube 124 can be rigid or flexible. Reservoir 121 is filled with an in-situ hardenable material 150 in an injectable state. Referring now to FIG. 10C, injection device 120 is shown releasably attached to preformed element 130. Preformed element 130 is positioned appropriately, such that shank 131 is partially supported by pilot hole 110 and partially positioned within bone cavity 112. Distal apertures 134 are positioned within bone cavity 112 in preparation for the injection of in-situ hardenable material 150.

Referring now to FIG. 10D, a detailed sectional view is shown to include the injection of in-situ hardenable material 150 into bone cavity 112. The stop 128 of injection device 120 abuts against head 136 to hold preformed element 130 in place and to place tip 126 in a suitable position adjacent to distal apertures 134. Within passage 133, in-situ hardenable material 150 flows through tube 124, and is released from tip 126 to flow in directly contact with passage 133 prior to flowing through distal apertures 134. Injection of in-situ hardenable material 150 flows through distal apertures 134 and enters the large bone cavity 112 at a relatively low pressure. In reference to prior-art, higher pressure is required to inject in-situ hardenable materials directly into cancellous bone, or into narrow interstitial spaces between bone and implant. The ability of the present invention to inject at lower pressure results in a broader spectrum of potential in-situ hardenable materials. Many of these materials have higher viscosity, and can be generally described as pastes. Injection of in-situ hardenable materials at lower pressures also allows for more effective injection over greater distances, more effective injection of through smaller diameter tubes, and the potential use of simpler, low-pressure injection systems (e.g., syringes). Further, lower pressures are advantageous because it decreases the potential of in-situ hardenable materials migrating to unintended areas.

Figure 10E:
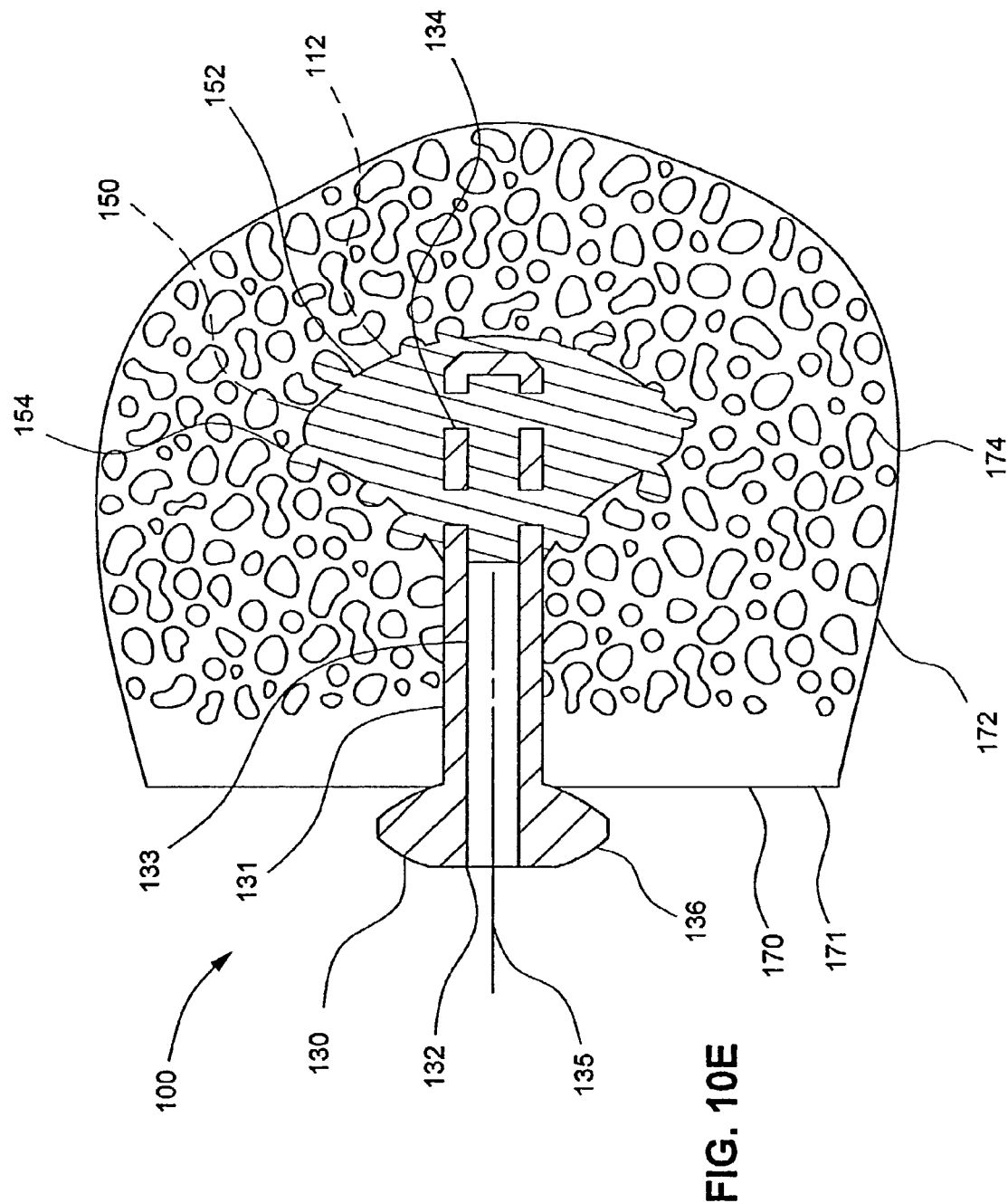

Referring now to FIG. 10E, bone fastener 100 is shown to include preformed element 130 and in-situ formed anchor 152, the latter is the result of hardening of the in-situ hardenable material 150. In an interlocking manner, in-situ hardenable material 150 hardens within bone cavity 112, throughout distal apertures 134 and partially within passage 133. In-situ formed material 150 has an inherent means for hardening to a non-flowing state, to include chemical reaction, cooling, or light-curing. Anchor-bone interlocks 154 are shown to extend from in-situ formed anchor 152 to fill, or partially fill adjacent bone pores 174. Cancellous bone pores 174 are interconnecting and the extent of anchor-bone interlocks 154 is dependent on numerous factors, to include bone pore 174 size, injection pressure, and the viscosity of the in-situ hardenable material 150.

Figure 11A:
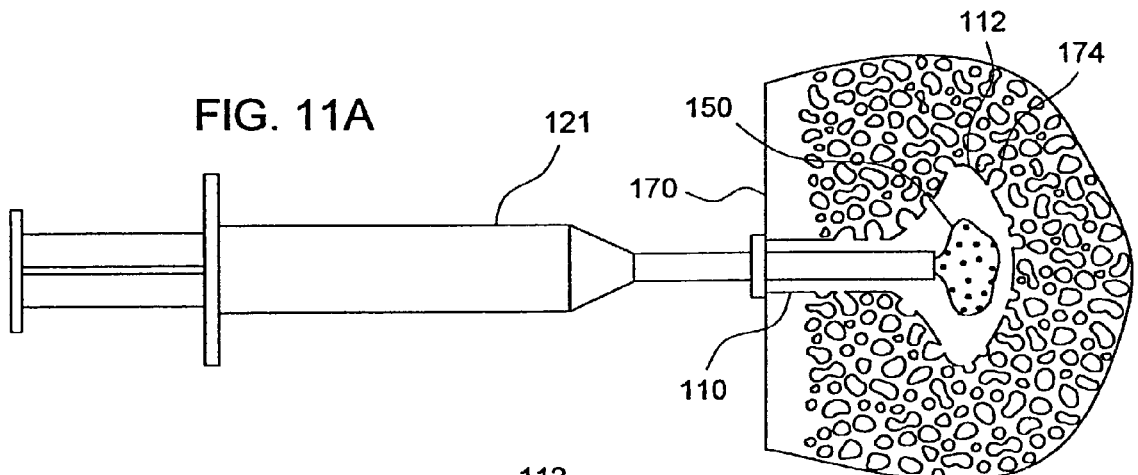
FIGS. 11A to 11C are in-situ sectional views depicting a second preferred method of implanting the bone fastener depicted in FIGS. 1B to 1C.
Figure 11B:
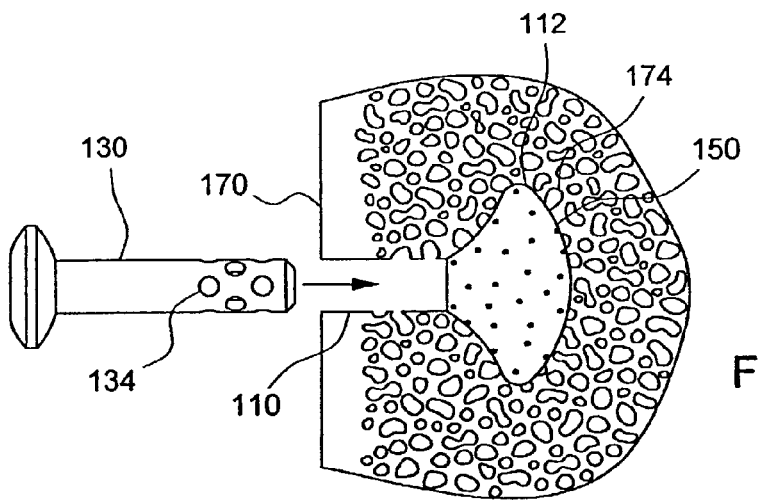
Figure 11C:
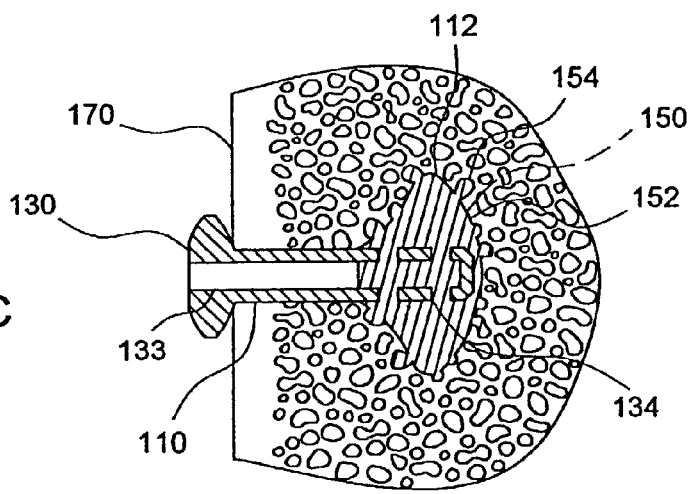

A second preferred method is depicted in FIGS. 11A to 11C. As stated previously, a second preferred method teaches an alternate sequence, first, injecting an in-situ hardenable material directly into a bone cavity, secondly, embedding a preformed element within the in-situ hardenable material. Referring now to FIG. 11A, injection device 121 injects in-situ hardenable material 150 into bone cavity 112. Referring now to FIG. 11B, in-situ hardenable material substantially fills bone cavity 112. In-situ hardenable material 150 can also reside within adjacent bone pores 174. Prior to hardening of in-situ hardenable material 150, a preformed element 130 is passed into pilot hole 110 and a portion of the preformed element 130 is embedded in in-situ hardenable material 150. Distal apertures 134 and passage 133 will fill, or partially fill with in-situ hardenable material 150 in an interlocking manner. Like a piston, embedding preformed element 130 into in-situ hardenable material 150 can also cause filling or partial filling of cancellous bone pores 174 adjacent to bone cavity 112. In-situ formed anchor 152 and anchor-bone interlocks 154 are created when in-situ hardenable material 150 transforms to a hardened state. This method can be applied to all preferred embodiments previously discussed.

A special case of the second preferred method relates to preformed elements with a screw thread, for example, preformed element 430 depicted in FIG. 4 and preformed element 530 depicted in FIG. 5. If in-situ hardenable material is allowed to harden prior to the insertion of a threaded preformed element, then the preformed element can be inserted with conventional methods associated with threading a bone screw into a solid.

Figure 12:
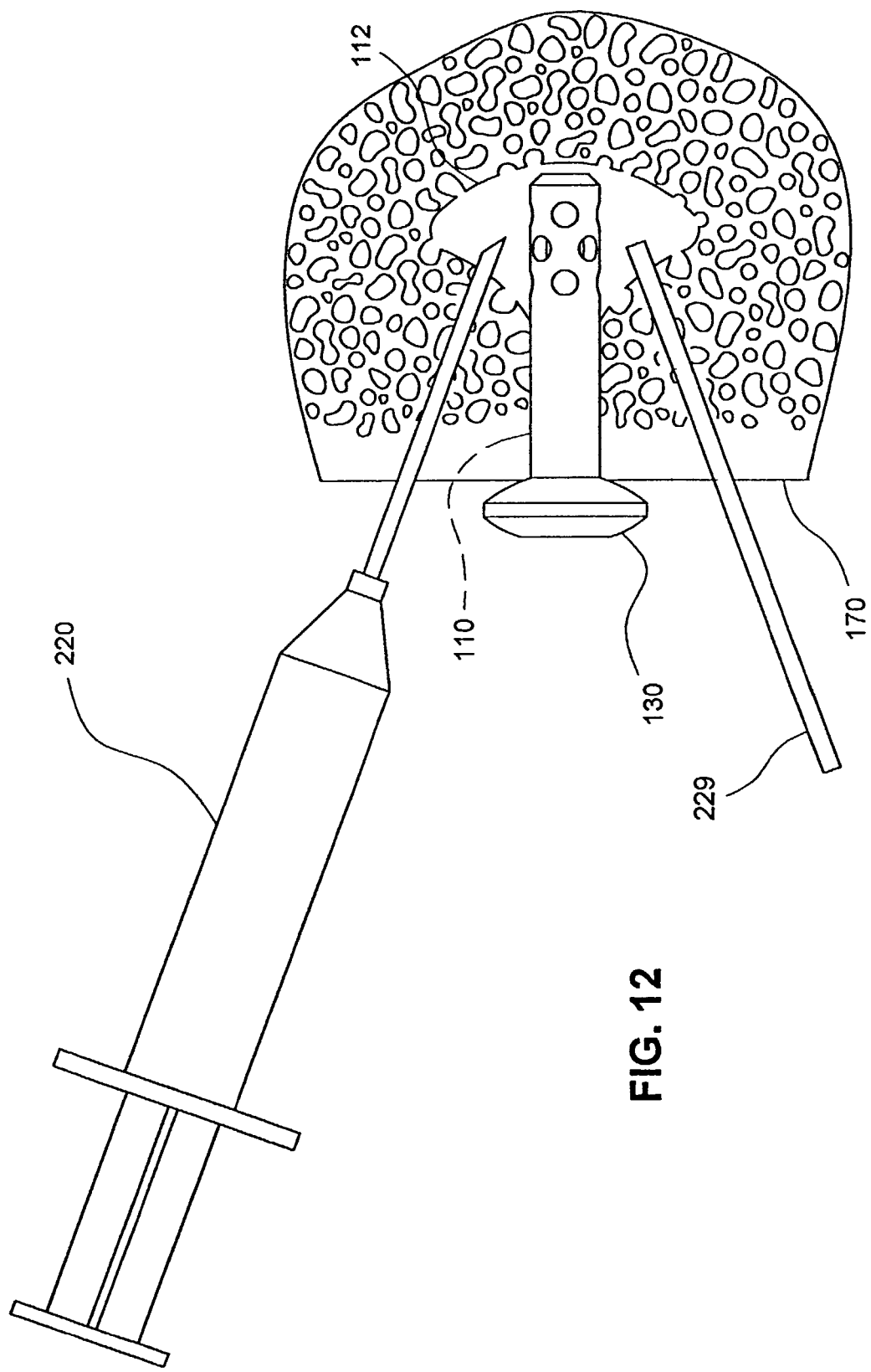
FIG. 12 is an in-situ sectional view depicting alternate preferred methods for material flow into a bone cavity and out of a bone cavity.

Previous discussion of methods establishes several fundamental steps of orthopaedic fixation with an in-situ formed anchor; however, variations thereof, and additional steps are also within the spirit of the present invention. For example, a bone cavity, to serve as a mold for an in-situ formed anchor can have multiple access holes and numerous devices can be used in communication with the bone cavity. Referring now to FIG. 12, in-situ sectional view is shown of bone 170 prepared with pilot hole 110 and bone cavity 112. Preformed element 130 is appropriately positioned within pilot hole 110 and bone cavity 112. Syringe 220 can be used to inject matter into bone cavity 112, such as, an in-situ hardenable material, a component of an in-situ hardenable material, or medicine. Alternatively, syringe 220 can be used in a suction mode to remove matter from bone cavity 112, such as blood. Similarly, drain tube 229 can be used to vent or drain matter from bone cavity 112, such as blood. In addition, preformed element 130 can be adapted for the flow of material into bone cavity 112 and out of bone cavity 112 for a variety of purposes to include suction and irrigation of a bone cavity or the administration of medicine.

Figure 13A:
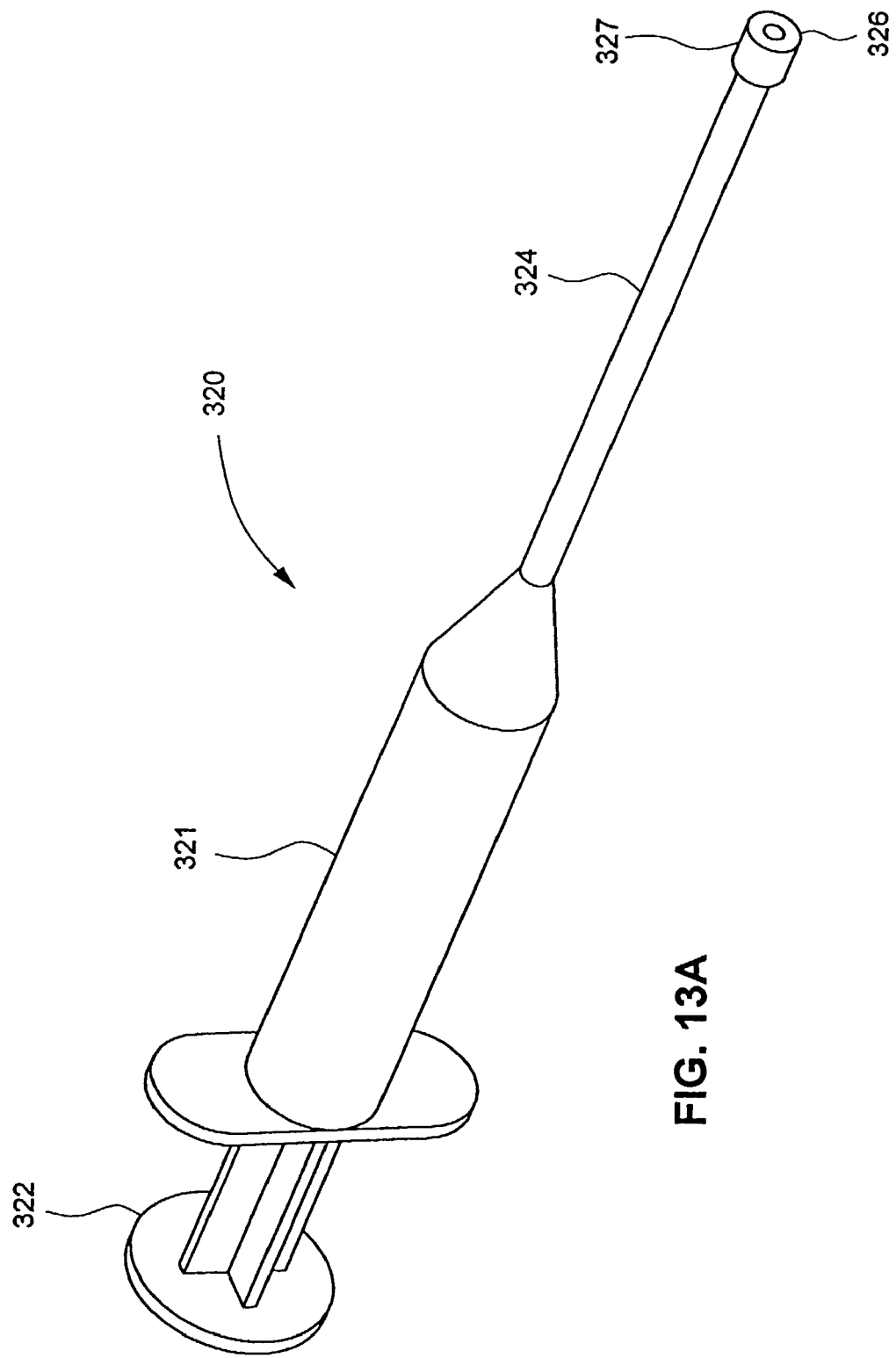
FIG. 13A is a perspective view of an injection device. In conjunction with the preformed element depicted in FIGS. 1A to 1C, a valve-flange is used to control the flow of materials into a bone cavity and out of a bone cavity.
Figure 13B:
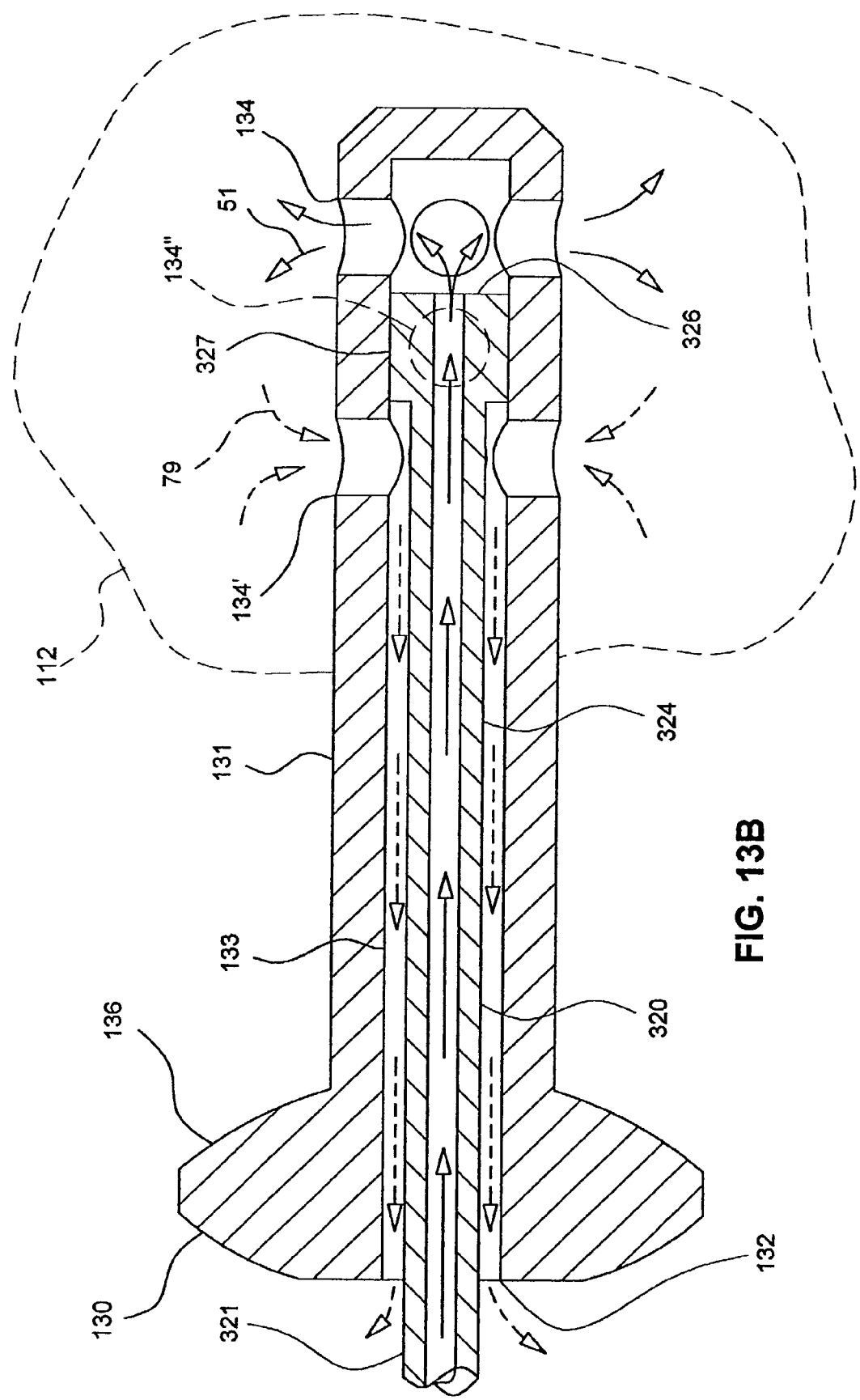
FIG. 13B is a detailed sectional view of the valve-flange within the preformed element.

A preferred embodiment of an injection device includes a valve-flange adapted to control the flow of matter from a bone cavity. Referring now to FIG. 13A, injection device 320 is a syringe-like device comprised of a reservoir body 321, plunger 322, tube 324, tip 326, and valve-flange 327. Referring now to FIG. 13B, a detailed sectional view of the injection device is shown positioned within preformed element 130. Valve-flange 327 is selectively positioned with respect to distal apertures 134, 134', 134". With respect to bone cavity 112, inflow arrows 51 show the flow of matter through tip 326, into passage 133, through distal apertures 134, and into bone cavity 112. Outflow arrows 79 show the flow of matter out of bone cavity 112, entering the passage through distal apertures 134' and flowing within passage 133, but external to tube 324. Therefore, pressures produced by injection device 320 can cause material to simultaneously flow into bone cavity 112 and out of bone cavity 112. Further, the valve-flange 327 is positioned to block flow of matter from distal apertures 134". An operator can selectively position the valve-flange 327 within the distal apertures 134, 134', 134" as a means to control flow. As an example, inflow arrows 51 can represent in-situ hardenable material injected into bone cavity 112, and outflow arrows 79 can represent blood simultaneously drained from bone cavity 112. An injection device adapted with a valve-flange can be used for a variety of other purposes to include suction and irrigation of a bone cavity or the administration of medicine.

From the description above, a number of advantages of the present invention become evident. An in-situ formed anchor establishes a broad foundation, securely fastening an implant to osteoporotic cancellous bone in an interlocking manner. Orthopaedic implant fixation with an in-situ formed anchor can be applied to a wide range of orthopaedic implants and applications. Those skilled in the art can envision retrofitting existing implant systems with the present invention. Relatively low pressures associated with distributing an injectable material within a bone cavity will allow in-situ hardenable materials to be delivered more effectively. The use of an injectable, in-situ hardenable materials also allow the present invention to be adapted to minimally invasive surgical techniques.

The preferred embodiments and preferred methods presented in this disclosure are examples. Those skilled in the art can develop modifications and variants that do not depart from the spirit and scope of the present invention. For example, multiple preformed elements can interlock with a single in-situ formed anchor. Thus, the scope of the invention should be determined by the appended claims and their legal equivalents, rather than by the examples given.

What is claimed is:

1. A method for the fixation of an orthopaedic implant in bone, wherein the orthopaedic implant is at least comprised of a preformed element and an in-situ formed anchor, the method comprising the steps of:

(a) forming in the bone a pilot hole with entry in bone, the pilot hole having a first diameter;

(b) forming in the bone a cavity connected to said pilot hole, said cavity having a second diameter that is substantially larger than the first diameter of said pilot hole, wherein said cavity is distal to the entry in bone;

(c) positioning a preformed element within said pilot hole and said cavity, said preformed element comprising:
 a shank having a length, a proximal end and a distal end, the length of said shank being sized so that the distal end of said shank extends into said cavity when said shank is positioned within said pilot hole;
 a proximal aperture disposed at the proximal end of said shank;
 a distal aperture disposed at the distal end of said shank; and
 a passage extending within said shank from said proximal aperture to said distal aperture; and
 one or more interlocking elements which are at least partially within the cavity, wherein there is a substantial space between the one or more interlocking elements and the boundary of the cavity;

(d) injecting a hardenable material in a flowable state into said proximal aperture so that said hardenable material in a flowable state flows through said passage and flows out of said distal aperture to at least partially fill said cavity;

(e) allowing said hardenable material to transition from a flowable state to a hardened state within said cavity for forming an in-situ formed anchor, wherein a diameter of the in situ formed anchor is substantially larger than said first diameter of said pilot hole, thereby fixing the orthopaedic implant to the bone.

2. The method of claim 1 wherein the hardenable material is selected from the group consisting of bone cement, polymethylmethacrylate-based bone cement, load-bearing polymer, synthetic bone substitute, thermoplastic, thermosetting polymer and combinations thereof.

3. The method of claim 1 wherein the preformed element is rigid and made of material selected from the group consisting of one or more metals, polymers, ceramics, and composites.

4. The method of claim 1 wherein the interlocking elements are selected from the group consisting of surface treatments, flanges, serrations, screw threads, holes, slots, grooves, flutes, dimples, and combinations thereof.

5. The method of claim 1 wherein the method is adapted to one of the group selected from a compression hip system, intramedullary nail system, suture anchor, and combinations thereof.

6. The method of claim 1 wherein the method stabilizes fractures.

7. The method of claim 1 wherein the in-situ anchor has a diameter larger than that of the preformed element.

8. A method for the fixation of an orthopaedic implant in bone, wherein the orthopaedic implant is at least comprised of a preformed element and an in-situ formed anchor, the method comprising the steps of:

forming a pilot hole with entry in bone, wherein the pilot hole has a first diameter;

forming in the bone a cavity having a diameter larger than the first diameter of the pilot hole, wherein the cavity is connected to the pilot hole and distal to the entry in bone;

positioning a preformed element at least partially within said cavity, wherein there is a substantial space between a distal portion of the preformed element and the cavity boundary and wherein the distal portion of the preformed element is in the cavity, said preformed element comprising:
a shank having a diameter, a length, a proximal portion and distal portion, the length of said shank being sized so that the distal portion of said shank is at least partially within said cavity;
a passage extending within said shank from said proximal portion to said distal portion; and
one or more interlocking elements which are at least partially within the cavity, wherein there is a substantial space between the one or more interlocking elements and the cavity boundary;
injecting a hardenable material in a flowable state into said passage at said proximal portion so that said hardenable material in a flowable state flows through said passage and flows out of the distal portion of said shank and the one or more interlocking elements and into the cavity;
allowing said hardenable material to harden while in contact with the one or more interlocking elements, thereby forming an in-situ formed anchor in an interlocking manner with said preformed element, wherein the in-situ formed anchor has a diameter substantially larger than the first diameter of the pilot hole, thereby fixing the orthopaedic implant to the bone.

9. The method of claim 8 wherein the method is adapted to one of the group selected from compression hip system, intramedullary nail system, suture anchor, and combinations thereof.

10. The method of claim 8 wherein the method stabilizes fractures.

11. The method of claim 8 wherein the hardenable material is selected from the group consisting of bone cement, polymethylmethacrylate-based bone cement, load-bearing polymer, synthetic bone substitute, thermoplastic, thermosetting polymers and combinations thereof.

12. The method of claim 8 wherein the preformed element is rigid and made of material selected from the group consisting of one or more metals, polymers, ceramics, and composites.

13. The method of claim 8 wherein the one or more interlocking elements are selected from the group consisting of apertures, surface treatments, flanges, serrations, cannulated bone screws, non-cannulated bone screws, screw threads, holes, slots, grooves, flutes, dimples.

14. A system for the fixation of an orthopaedic implant in bone, wherein the orthopaedic implant is at least comprised of a preformed element and an in-situ formed anchor, the system comprising:
a pilot hole with entry in bone;
a cavity in bone, wherein the cavity is connected to the pilot hole, the cavity is distal to the pilot hole entry, and said cavity has a substantially larger diameter than the pilot hole;
a preformed element, said preformed element comprising:
a shank having a length, a proximal portion and a distal portion, the length of said shank being sized so that said distal portion is positioned and remains at least partially within the cavity in the bone leaving a substantial space between the distal portion and the boundary of the cavity;
a passage extending within said shank from said proximal portion to said distal portion; and
one or more interlocking elements which are at least partially within the cavity, wherein there is a substantial space between the one or more interlocking elements and at least a portion of the cavity; and
an injectable and a hardenable material for forming an in-situ anchor that interlocks with the one or more interlocking elements, wherein the in-situ anchor fills the cavity and has diameter substantially larger than that of the preformed element.

15. The system of claim 14 wherein the hardenable material is selected from the group consisting of bone cement, polymethylmethacrylate-based bone cement, loadbearing polymer, synthetic bone substitute, thermoplastic, thermosetting polymers and combinations thereof.

16. The system of claim 14 wherein the preformed element is rigid and made of material selected from the group consisting of one or more metals, polymers, ceramics, and composites.

17. The system of claim 14 wherein the one or more interlocking elements are selected from the group consisting of apertures, surface treatments, flanges, serrations, cannulated bone screws, non-cannulated bone screws, threaded screws, non threaded screws, holes, slots, grooves, flutes, dimples.

18. The system of claim 14 wherein the system is adapted to one of the group selected from compression hip system, intramedullary nail system, fracture, suture anchor, and combinations thereof.

19. The system of claim 14 wherein the system stabilizes fractures.

20. The system of claim 14 wherein the injectable and hardenable material is in a flowable state.

21. The system of claim 14 wherein the injectable and hardenable material is in a hardened state.

22. A method for the fixation of an orthopaedic implant in bone, wherein the orthopaedic implant is at least comprised of a preformed element and an in-situ formed anchor, the method comprising the steps of:
forming a pilot hole entry in bone;
forming a pilot hole having a first diameter in the bone;
forming in the bone a cavity having a diameter larger than the first diameter of the pilot hole, wherein pilot hole and cavity are connected and the cavity is positioned distal to the pilot hole entry in bone;
injecting a hardenable material in a flowable state into said cavity; and
positioning a preformed element at least partially within said cavity, said preformed element comprising:
a shank having a diameter, a length, a proximal portion, and one or more interlocking elements associated with a distal portion of the shank, the length of said shank being sized so that the distal portion remains within said cavity and the one of more interlocking elements are in contact with the hardenable material in a flowable state, wherein there is a substantial space between the one or more interlocking elements and a portion of the cavity boundary;
allowing said hardenable material to transition from a flowable state to a hardened state while in contact with the one or more interlocking elements, thereby forming an in-situ formed anchor interlocked with said preformed element, the in-situ formed anchor having a diameter substantially larger than the diameter of the preformed element and substantially larger than the first diameter of the pilot hole, thereby fixing the orthopaedic implant to the bone.

23. The method of claim 22 wherein said hardenable material in a flowable state flows into said cavity.

24. The method of claim 22 wherein said cavity is connected to a pilot hole, said cavity having a diameter that is substantially larger than that of said pilot hole.

25. A method for the fixation of an orthopaedic implant in bone, wherein the orthopaedic implant is at least comprised of a preformed element and an in-situ formed anchor, the method comprising the steps of:
  forming a pilot hole in the bone with a pilot hole entry, the pilot hole having a first diameter;
  forming in the bone a cavity connected to the pilot hole having a diameter larger than the first diameter of the pilot hole wherein the cavity is distal to the pilot hole entry;
  positioning both a hardenable material in a flowable state and a preformed element at least partially within said cavity, said preformed element comprising:
    a body having a proximal portion and a distal portion, wherein the distal portion has one or more interlocking elements adapted for flow of the hardenable material in a flowable state, the distal portion of said body positioned within said cavity, wherein there is substantial space between the one or more interlocking elements and a portion of the boundary of the cavity;
  allowing said hardenable material to harden while positioned in contact with said one or more interlocking elements, thereby forming an in-situ formed anchor interlocked with said preformed element, wherein the in-situ formed anchor has a diameter substantially larger than the first diameter of the pilot hole, thereby fixing the orthopaedic implant to the bone.

26. The method of claim 25 wherein the interlocking elements are selected from the group consisting of apertures, passages, surface treatments, flanges, serrations, screw threads, holes, slots, grooves, flutes, dimples.

* * * * *